(12) United States Patent
Kanamori et al.

(10) Patent No.: US 9,575,178 B2
(45) Date of Patent: Feb. 21, 2017

(54) BEAMFORMING METHOD AND ULTRASONIC DIAGNOSTIC APPARATUS

(71) Applicant: KONICA MINOLTA, INC., Tokyo (JP)

(72) Inventors: Takeo Kanamori, Osaka (JP); Yasuhito Watanabe, Osaka (JP); Mineo Tsushima, Kyoto (JP)

(73) Assignee: KONICA MINOLTA, INC., Tokyo (JP)

( * ) Notice: Subject to any disclaimer, the term of this patent is extended or adjusted under 35 U.S.C. 154(b) by 610 days.

(21) Appl. No.: 14/086,441

(22) Filed: Nov. 21, 2013

(65) Prior Publication Data

US 2014/0078866 A1 Mar. 20, 2014

Related U.S. Application Data

(63) Continuation of application No. PCT/JP2013/002850, filed on Apr. 26, 2013.

(30) Foreign Application Priority Data

Apr. 27, 2012 (JP) ................. 2012-104166

(51) Int. Cl.
*G01S 15/00* (2006.01)
*G01S 15/02* (2006.01)
(Continued)

(52) U.S. Cl.
CPC ............. *G01S 15/02* (2013.01); *A61B 8/4461* (2013.01); *A61B 8/4483* (2013.01);
(Continued)

(58) Field of Classification Search
USPC ....................................................... 367/138
See application file for complete search history.

(56) References Cited

U.S. PATENT DOCUMENTS 6,126,604 A * 10/2000 Bae ............................... 600/454
6,251,074 B1 * 6/2001 Averkiou et al. ............. 600/447
(Continued)

FOREIGN PATENT DOCUMENTS

JP 10-127635 5/1998
JP 11-123191 5/1999
(Continued)

OTHER PUBLICATIONS

Masayasu Ito et al., Chiyouompa shindan souchi (ultrasonic diagnostic device) ["Chouonpa shindan souchi (ultrasonic diagnostic apparatus)",] Corona Publishing Co., Ltd., 2002.
(Continued)

*Primary Examiner* — James Hulka
(74) *Attorney, Agent, or Firm* — Holtz, Holtz & Volek PC

(57) ABSTRACT

A beamforming method includes: generating a main beam signal by performing, with a focus on a first region, a delay and sum operation on receiving echo signals; generating a sub beam signal which has a low sensitivity to ultrasound signals reflected off the first region; and generating a narrow beam signal by (i) calculating a coefficient for narrowing an angle of the main beam signal, and (ii) multiplying the main beam signal by the coefficient, wherein in the generating of a sub beam signal, the sub beam signal is generated using a differential signal that is a difference between two beam signals each of which is generated by performing a delay and sum operation on the receiving echo signals, with a focus on a corresponding one of two regions of a subject which are different from the first region and are different from each other.

11 Claims, 16 Drawing Sheets

(51) Int. Cl.
*A61B 8/00* (2006.01)
*A61B 8/08* (2006.01)
*G01S 7/52* (2006.01)
*G01S 15/89* (2006.01)
*G10K 11/34* (2006.01)

(52) U.S. Cl.
CPC ........ *A61B 8/5207* (2013.01); *G01S 7/52047* (2013.01); *G01S 15/8915* (2013.01); *G10K 11/346* (2013.01)

(56) References Cited

U.S. PATENT DOCUMENTS

| | | | |
|---|---|---|---|
| 6,705,993 | B2* | 3/2004 | Ebbini et al. ................ 600/443 |
| 7,921,717 | B2* | 4/2011 | Jackson et al. ................ 73/602 |
| 8,045,777 | B2 | 10/2011 | Zwirn |
| 8,241,216 | B2* | 8/2012 | Loftman et al. ............. 600/443 |
| 8,290,061 | B2* | 10/2012 | Sang et al. ................ 375/240.24 |
| 2003/0210179 | A1* | 11/2003 | Dizaji et al. ................ 342/159 |
| 2006/0173313 | A1 | 8/2006 | Liu et al. |
| 2007/0047743 | A1 | 3/2007 | Taenzer et al. |
| 2008/0262352 | A1 | 10/2008 | Zwirn |
| 2009/0016163 | A1* | 1/2009 | Freeman et al. ............. 367/103 |
| 2009/0141957 | A1 | 6/2009 | Yen et al. |
| 2009/0171213 | A1* | 7/2009 | Savord ........................ 600/447 |
| 2012/0157851 | A1 | 6/2012 | Zwirn |
| 2012/0289835 | A1 | 11/2012 | Hwang |

FOREIGN PATENT DOCUMENTS

| | | |
|---|---|---|
| JP | 2003-325507 | 11/2003 |
| JP | 2008-526291 | 7/2006 |
| JP | 2006-204923 | 8/2006 |
| JP | 2009-506683 | 2/2009 |
| JP | 2010-158374 | 7/2010 |
| WO | 2006/070362 | 7/2006 |
| WO | 2007/025265 | 3/2007 |
| WO | 2011/057252 | 5/2011 |

OTHER PUBLICATIONS

International Search Report issued in International Application No. PCT/JP2013/002850 on May 28, 2013.
Extended European Search Report dated Apr. 7, 2015, issued in counterpart European Application No. 13781523.9.

* cited by examiner

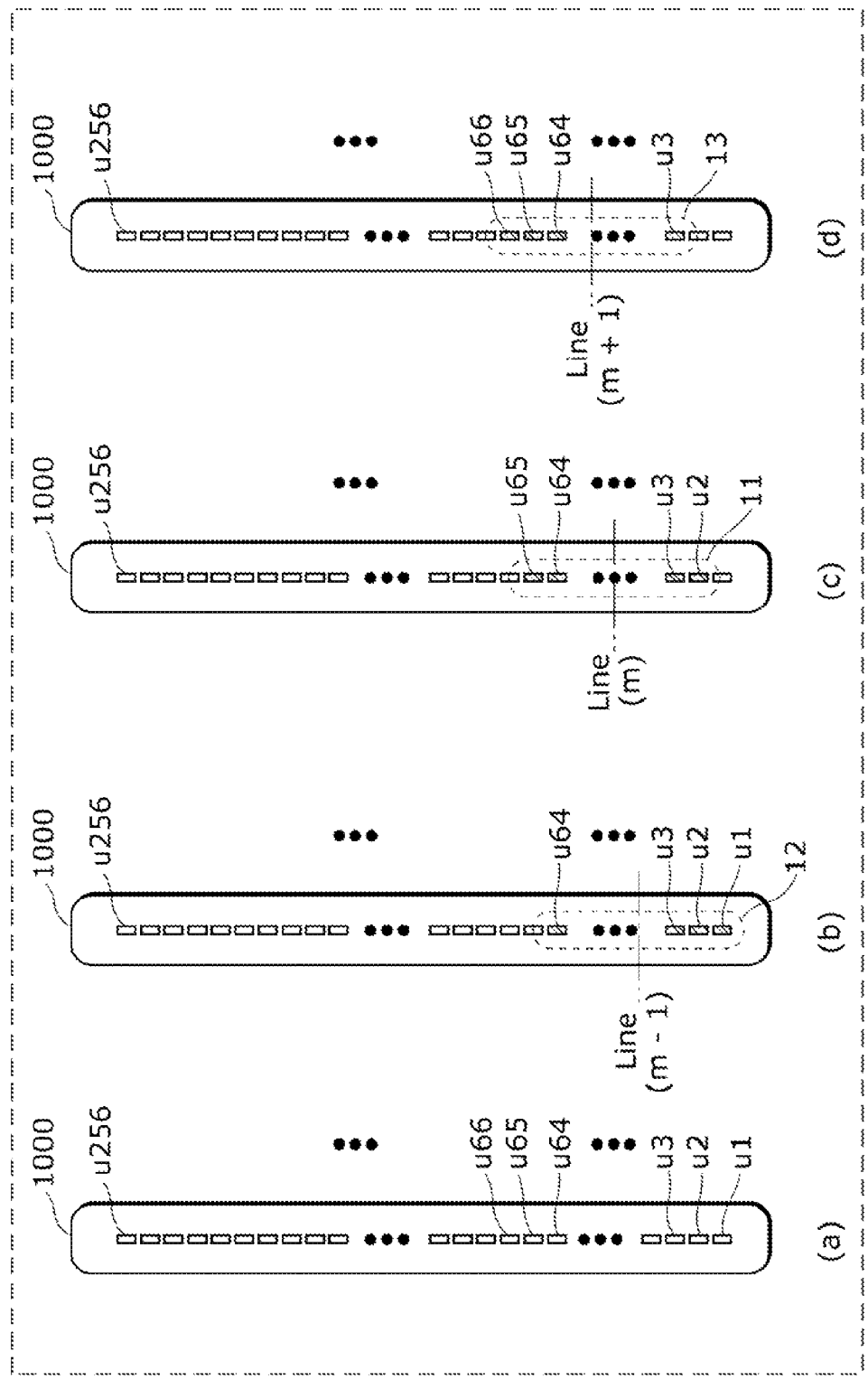

BEAMFORMING METHOD AND ULTRASONIC DIAGNOSTIC APPARATUS

CROSS REFERENCE TO RELATED APPLICATION

This is a continuation application of PCT International Application No. PCT/JP2013/002850 filed on Apr. 26, 2013, designating the United States of America, which is based on and claims priority of Japanese Patent Application No. 2012-104166 filed on Apr. 27, 2012. The entire disclosures of the above-identified applications, including the specifications, drawings and claims are incorporated herein by reference in their entirety.

FIELD

One or more exemplary embodiments disclosed herein relate generally to beamforming methods and ultrasonic diagnostic apparatuses.

BACKGROUND

Conventional ultrasonic diagnostic apparatuses employ, as an ultrasound beamforming method for receiving, a method generally referred to as a delay and sum method (e.g., see Non Patent Literature (NPL) 1).

CITATION LIST

Non Patent Literature

[NPL 1]
"Chouonpa shindan souchi (ultrasonic diagnostic apparatus)", Masayasu Ito, Takashi Motizuki CORONA PUBLISHING CO., LTD Aug. 26, 2002, pp. 42-45)

SUMMARY

Technical Problem

However, when beamforming is performed using a delay and sum method as with conventional ultrasonic diagnostic apparatuses, a beam which corresponds to a main lobe of a receiving beam cannot be sufficiently narrowed (i.e., cannot increase directivity) in a region to be observed, which leads to a situation where resolution of the image depicting receiving signals of ultrasound waves does not improve.

One non-limiting and exemplary embodiment provides a beamforming method which makes it possible to enhance the resolution of an ultrasound diagnostic image to be obtained.

Solution to Problem

In order to solve the above-described problem, one general aspect, the techniques disclosed here feature a beamforming method for generating a beam signal from echo signals generated by a plurality of receiving elements receiving ultrasound signals reflected off a subject, the method including: generating a main beam signal by performing a delay and sum operation on receiving echo signals obtained from the receiving elements, using, as a focal point, a first region of the subject; generating, from the receiving echo signals, a sub beam signal which, compared to the main beam signal, has a low sensitivity to ultrasound signals reflected off the first region; and generating a narrow beam signal by (i) calculating a coefficient for narrowing an angle of the main beam signal, and (ii) multiplying the main beam signal by the coefficient, the coefficient being determined based on the main beam signal and the sub beam signal, wherein in the generating of a sub beam signal, the sub beam signal is generated using a differential signal that is a difference between two beam signals each of which is generated by performing a delay and sum operation on the receiving echo signals, using, as a focal point, a corresponding one of two regions of the subject which are different from the first region and are different from each other.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

A beamforming method according to one or more exemplary embodiments or features disclosed herein enhances the resolution of an ultrasound diagnostic image to be obtained.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 3 is a diagram showing a positional relationship between a receiving unit and a receiving element array according to Embodiment 1.

DESCRIPTION OF EMBODIMENTS

Underlying Knowledge Forming Basis of the Present Disclosure

In relation to the beamforming method disclosed in the Background section, the inventors have found the following problem.

Figure 15:
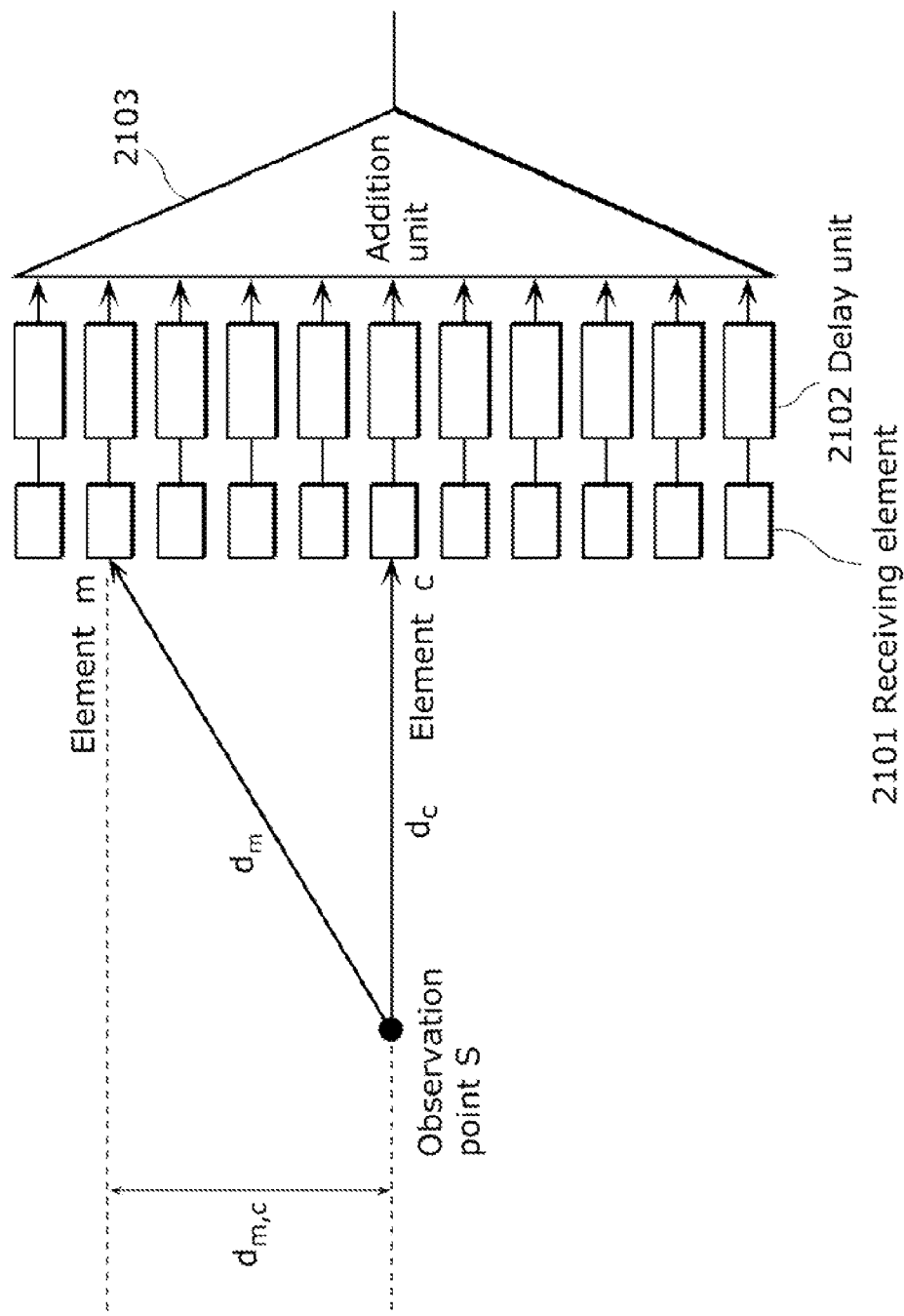
FIG. 15 is a diagram showing a beamforming method according to a relevant technique.

FIG. 15 schematically shows a delay and sum method employed by an ultrasonic diagnostic apparatus according to a relevant technique of the present disclosure.

The ultrasonic diagnostic apparatus which executes the delay and sum method shown in FIG. 15 includes: receiving elements 2101 which are elements that receive ultrasound waves; a delay unit 2102 which is associated with a corresponding one of the receiving elements and performs delay processing on a signal; and an addition unit 2103 which sums output signals of the delay units 2102.

According to the delay and sum method, on the signals received by the receiving element 2101, the delay unit 2102 performs the delay processing for each of the elements. After this, the addition unit 2103 sums the signals, which have undergone the delay processing, and outputs the result. With this, the ultrasonic diagnostic apparatus receives ultrasound waves emitted by an observation point S.

However, when beamforming is performed using a delay and sum method as with the above-described ultrasonic diagnostic apparatus, a beam which corresponds to a main lobe of a receiving beam cannot be sufficiently narrowed (i.e., cannot increase directivity) in a region to be observed, which results in a situation where resolution of the image depicting receiving signals of ultrasound does not improve. Furthermore, a noise signal from the region other than the region to be observed (i.e., an echo signal that is not from the region to be observed) mixes into a beam which represents a characteristic of the observation region, causing a decrease in S/N ratio resulting in a problem of degradation of the quality of displayed image (a problem concerning a side lobe).

The present disclosure solves the above described problems, and has an object to provide a beamforming method and the like which can realize a high-quality received image containing less noise, and enhance the resolution of an ultrasound diagnostic image.

The beamforming method according to the present disclosure makes it possible to enhance the resolution of an ultrasound diagnostic image to be obtained. More specifically, the configuration according to the present disclosure makes it possible to realize narrowing of beam (narrowing of angle) compared to the above-described ultrasonic diagnostic apparatus. The resolution and the quality of an image, which is generated using a signal that has been beamformed using the beamforming method according to the present disclosure, improve.

In order to solve the above-described problem, a beamforming method according to an exemplary embodiment disclosed herein is a beamforming method for generating a beam signal from echo signals generated by a plurality of receiving elements receiving ultrasound signals reflected off a subject, the method including: generating a main beam signal by performing a delay and sum operation on receiving echo signals obtained from the receiving elements, using, as a focal point, a first region of the subject; generating, from the receiving echo signals, a sub beam signal which, compared to the main beam signal, has a low sensitivity to ultrasound signals reflected off the first region; and generating a narrow beam signal by (i) calculating a coefficient for narrowing an angle of the main beam signal, and (ii) multiplying the main beam signal by the coefficient, the coefficient being determined based on the main beam signal and the sub beam signal, wherein in the generating of a sub beam signal, the sub beam signal is generated using a differential signal that is a difference between two beam signals each of which is generated by performing a delay and sum operation on the receiving echo signals, using, as a focal point, a corresponding one of two regions of the subject which are different from the first region and are different from each other.

With this beamforming method, the ultrasonic diagnostic apparatus can narrow an angle of sensitivity characteristic of the received beam signal. More specifically, with this beamforming method, an angle of the main beam signal obtained from a region of interest of a specimen (subject) is narrowed, by using two sub beam signals obtained from regions of the specimen which are different from the region of interest. Here, each of the two sub beam signals includes a signal obtained from the region of interest. Thus, by using a differential signal of the two sub beam signals, an ultrasonic diagnostic apparatus can generate a signal which has a blind spot of sensitivity in the region of interest of the main signal. Then, the angle of the main beam signal is narrowed by operating on the generated signal and the main beam signal. Thus, with this beamforming method, the ultrasonic diagnostic apparatus can enhance the resolution of the ultrasound diagnostic image to be obtained.

For example, in the generating of a sub beam signal, the sub beam signal may be generated by multiplying the main beam signal by the differential signal.

With this beamforming method, the ultrasonic diagnostic apparatus can narrow the angle of the blind spot of sensitivity of a signal generated from the sub beam signals. The angle of the main beam signal can be further narrowed by operating on the signal, which has the blind spot of sensitivity that has been narrowed, and the main beam signal. Thus, with this beamforming method, the ultrasonic diagnostic apparatus can further enhance the resolution of the ultrasound diagnostic image to be obtained.

For example, in the generating of a sub beam signal, the sub beam signal may be generated by multiplying the differential signal by the main beam signal multiplied by a predetermined constant a.

With this beamforming method, the ultrasonic diagnostic apparatus can adjust the degree of narrowing of angle of the blind spot of sensitivity of the signal which is generated from the sub beam signals. Thus, with this beamforming method, the ultrasonic diagnostic apparatus can adjust the degree of resolution enhancement of the ultrasound diagnostic image to be obtained.

For example, it may be that the predetermined constant a is determined for each distance between the first region and an element array which includes the receiving elements, and in the generating of a sub beam signal, the sub beam signal is generated by multiplying the differential signal by the main beam signal multiplied by the predetermined constant a, using the predetermined constant a which is determined based on a distance between (i) the first region used when the delay and sum operation is performed in the generating of a sub beam signal and (ii) the element array, the distance being a distance when the receiving echo signals are received.

With this beamforming method, the ultrasonic diagnostic apparatus can adjust, based on the depth of the region of interest of the specimen from the body surface of the specimen, the degree of narrowing of angle of the blind spot of sensitivity.

For example, the beamforming method may further include receiving a user operation for changing the predetermined constant a.

With this beamforming method, the ultrasonic diagnostic apparatus can adjust the degree of narrowing of angle of the blind spot of sensitivity, following an operation by a user. A propagation characteristic of ultrasound waves changes due to various factors. Thus, with a fine adjustment of the predetermined constant by the user, the ultrasonic diagnostic apparatus can adjust the degree of narrowing of angle of the blind spot of sensitivity more appropriately.

For example, it may be that the beamforming method further includes: generating partial main beam signals by dividing, based on a division frequency, the main beam signal into signals of respective frequency bands, the main beam signal being generated in the generating of a main beam; and generating partial sub beam signals by dividing, based on the division frequency, each of the two beam signals into signals of respective frequency bands, the two beams being generated in the generating of a sub beam signal, wherein in the generating of a narrow beam signal, the narrow beam signal is generated by (i) generating partial narrow beam signals that are the narrow beam signals of respective frequency bands, and (ii) adding up the generated partial narrow beam signals, the partial narrow beam signals each being generated by using a corresponding one of the partial main beam signals as the main beam signal, and using a corresponding one of the partial sub beam signals as the sub beam signal.

With this beamforming method, the ultrasonic diagnostic apparatus can divide the ultrasound waves received from the specimen for respective frequencies of the ultrasound waves, and perform, on the divided signal, the narrowing of angle in a similar manner as above. The receiving sensitivity is different for each frequency of ultrasound waves. Thus, with the above, the narrowing of angle for each frequency corresponding to the receiving sensitivity can be performed.

For example, it may be that the predetermined constant a is determined for each of the frequency bands, in the generating of a sub beam signal, the partial sub beam signal is generated by multiplying the differential signal by the partial main beam signal multiplied by the predetermined constant a, using the predetermined constant a which is determined based on the frequency band of each of the partial sub beam signals.

With this beamforming method, the ultrasonic diagnostic apparatus can divide ultrasound waves received from the specimen for the respective frequencies of the ultrasound waves, and perform, for each of the divided signals, narrowing of angle similar to the above using a predetermined constant.

For example, it may be that in the generating of a sub beam signal, the sub beam signal is generated by using, as the two regions, two regions each of which is equidistant from a center of an element array including the receiving elements and from the first region.

With this beamforming method, the ultrasonic diagnostic apparatus can generate a signal which has a blind spot of sensitivity in the region of interest of the specimen. The signals obtained by performing the delay and sum operation using, as a focal point, each of the two regions have an identical sensitivity at a position which corresponds to the region of interest. Thus, the differential signal of these signals have, at a position corresponding to the region of interest, a blind spot of sensitivity in which the sensitivity is 0. With this, the ultrasonic diagnostic apparatus can narrow the angle of the main beam signal more accurately.

For example, it may be that the receiving echo signals include a first receiving echo signal, a second receiving echo signal, and a third receiving echo signal which are received and generated by the receiving elements at a first time point, a second time point, and a third time point, respectively, the first time point, the second time point, and the third time point being three time points different from one another, in the generating of a main beam signal, the main beam signal is generated using, as the receiving echo signals, the first receiving echo signal, and in the generating of a sub beam signal, the sub beam signal is generated, using as the two beam signals, the second receiving echo signal and the third receiving echo signal.

With this beamforming method, the ultrasonic diagnostic apparatus can sequentially generate a main beam signal and a sub beam signal, and using the generated signals, the ultrasonic diagnostic apparatus can narrow the angle of the main beam signal.

Furthermore, an ultrasonic diagnostic apparatus according to an exemplary embodiment disclosed herein is an ultrasonic diagnostic apparatus that generates a beam signal from echo signals generated by a plurality of receiving elements receiving ultrasound signals reflected off a subject, the ultrasonic diagnostic apparatus including: a main beam generation unit configured to generate a main beam signal by performing a delay and sum operation on receiving echo signals obtained from the receiving elements, using, as a focal point, a first region of the subject; a sub beam generation unit configured to generate, from the receiving echo signals, a sub beam signal which, compared to the main beam signal, has a low sensitivity to ultrasound signals reflected off the first region; and a narrow beam generation unit configured to generate a narrow beam signal by (i) calculating a coefficient for narrowing an angle of the main beam signal, and (ii) multiplying the main beam signal by the coefficient, the coefficient being determined based on the main beam signal and the sub beam signal, wherein the sub beam generation unit is configured to generate the sub beam signal, using a differential signal that is a difference between two beam signals each of which is generated by performing a delay and sum operation on the receiving echo signals, using, as a focal point, a corresponding one of two regions of the subject which are different from the first region and are different from each other.

With this, the advantageous effect similar to the advantageous effect of the above beam forming method can be produced.

These genera and specific aspects may be implemented using a system, a method, an integrated circuit, a computer program, or a computer-readable recording medium, such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

Figure 1:
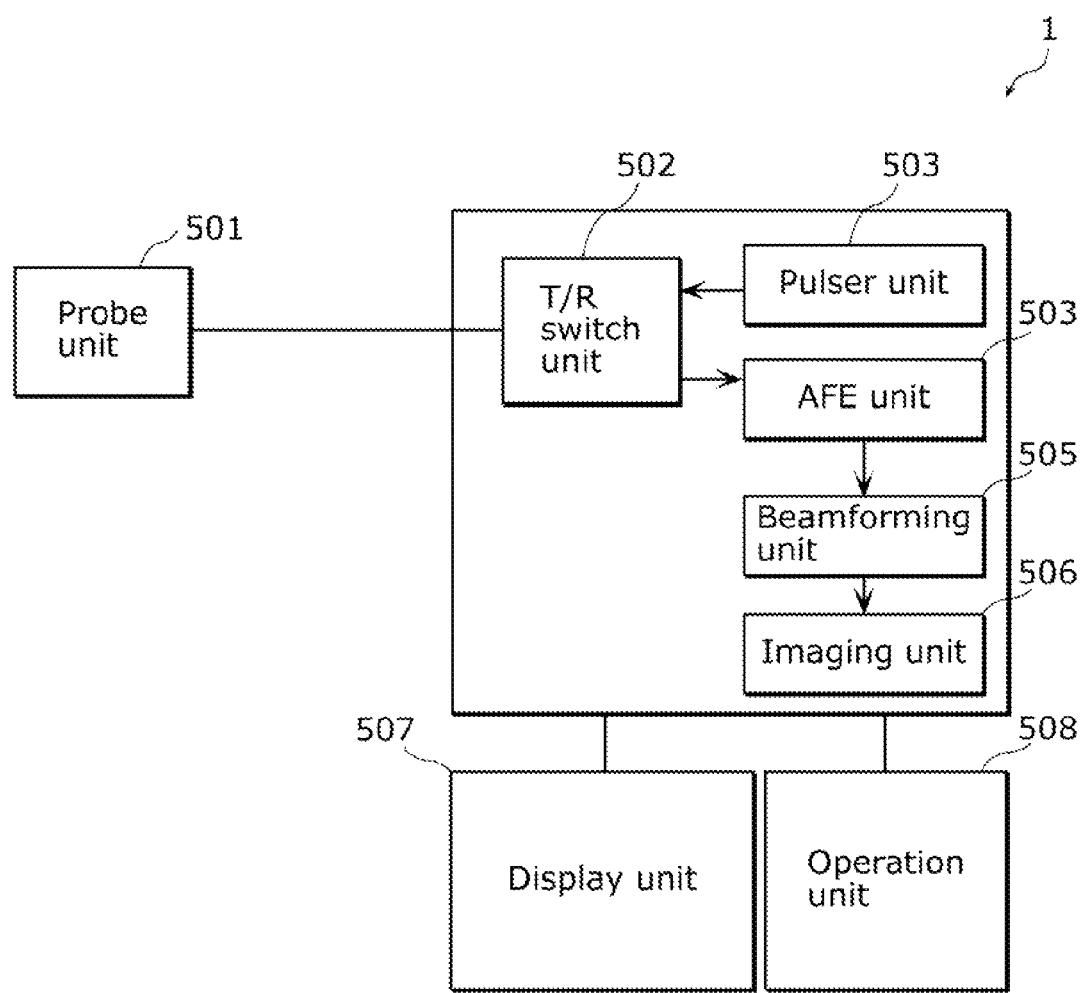
FIG. 1 is a configuration diagram of an ultrasonic diagnostic apparatus.

FIG. 1 shows an example of a configuration of an ultrasonic diagnostic apparatus 1 which realizes a beamforming method according to this embodiment.

The ultrasonic diagnostic apparatus 1 includes: a probe unit 501, a T/R switch unit 502, a pulser unit 503, an AFE unit 504, a beamforming unit 505, an imaging unit 506, a display unit 507, and an operation unit 508.

The probe unit 501 transmits ultrasound waves to a specimen (also referred to as a subject which is, for example, a body), and receives the ultrasound waves reflected off the specimen to generate receiving signals.

The T/R switch unit 502 electrically switches between a transmission signal to be transmitted to the probe unit 501 and a receiving signal to be received from the probe unit 501 in view of circuit protection.

The pulser unit 503 generates an electric signal which prompts the transmission of the ultrasound waves.

The AFE unit 504 receives the receiving signals generated by the probe unit 501 receiving reflected waves which are ultrasound waves generated as a result of the ultrasound waves being transmitted by the probe unit 501 and reflected off the specimen. Then, the AFE unit 504 performs processing including amplification of the receiving signals, and converts the receiving signals into a sequence of digital signals by analogue-to-digital conversion. The AFE unit 504 corresponds to what is called an analogue front end.

The beamforming unit 505 performs beamforming, by array signal processing on the digital signal sequence generated by the AFE unit 504. The beamforming corresponds to focusing processing performed on a region to be visualized.

The imaging unit 506 generates a display image (ultrasound diagnostic image) from the signals obtained by the beamforming unit 505.

The display unit 507 displays the display image generated by the imaging unit 506.

The operation unit 508 performs control and operation of processing performed by each of the above-described functional blocks. Furthermore, the operation unit 508 may receive operation made by a user and perform the control and operation.

The present disclosure has, in particular, a feature in the beamforming unit 505 which generates a beam signal used for generating an ultrasound diagnostic image through calculation of receiving signals of ultrasound waves. Note that, as for the structural elements other than the features of the present disclosure, structural elements of a conventional ultrasonic diagnostic apparatus can be used. Thus, in place of a beamforming unit according to the conventional ultrasonic diagnostic apparatus, the beamforming unit 505 according to the present disclosure may be introduced.

Note that, the ultrasonic diagnostic apparatus 1 according to the present disclosure is not limited to the ultrasonic diagnostic apparatus having the configuration shown in FIG. 1. For example, the T/R switch unit 502 may be omitted in the case where different elements are used as a transmission element and a reception element. Furthermore, the probe unit 501 may include the pulser unit 503 or the probe unit 501 may include the pulser unit 503 and the AFE unit 504. In addition, the probe unit 501 may include all the other functional blocks.

The following describes the beamforming unit 505 according to this embodiment.

The method described here is a method, which can be applied to an ultrasonic diagnostic apparatus, for sharpening the angle of the beam signal by using a main beam signal and a sub beam signal. The sub beam signal is for creating a blind spot of sensitivity in a target region in which the main beam signal has high receiving sensitivity. Note that, in the following, the beam signal, the main beam signal, and the sub beam signal are also referred to as a beam, a main beam, and a sub beam, respectively.

First, a feature of a subtraction-type beamformer is described. Note that, a method of combining the sub beams according to this embodiment can also be described that a subtraction-type beamformer, which is used as a beamformer for a microphone or the like that handles an acoustic signal in an audible range, is applied to an ultrasound diagnostic apparatus by improving shortcomings of the subtraction-type beamformer to suit the use by an ultrasonic diagnostic apparatus.

For the microphone or the like which handles an acoustic signal in an audible range, a method is available in which the angle of the beam is sharpen using a main beam and sub beams. The sub beam is for creating a blind spot of sensitivity in a direction in which the main beam has highest sensitivity. In this case, for the sub beam, a subtraction-type beamformer is used which can control the direction of the blind spot of sensitivity. The subtraction-type beamformer refers to a method that creates, in an arbitrary direction, the blind spot of sensitivity by performing subtraction on signals, which have undergone a phase adjustment, of two elements. This method is known to be sensitive to a phase accuracy of signals of elements or closeness of sensitivity (variation in sensitivity) of elements, and has a problem of sensitivity degradation in a sensitive region after beamforming. On the other hand, ultrasound waves have different speed of sound among various tissues that are propagation mediums in a body. Furthermore, ultrasound waves have non-linear property in propagating. Thus, signal correlation between elements of the ultrasonic diagnostic apparatus becomes small, which makes it difficult to create a blind spot of sensitivity in the target region with a simple subtraction-type beamformer. Furthermore, a signal is significantly attenuated during propagation in a body, and thus an effect from a problem of decreased sensitivity in the subtraction-type beamformer is significant. Thus, it is difficult to apply, to the ultrasonic diagnostic apparatus, the subtraction-type beamformer which directly performs subtraction on output from a microphone element.

This embodiment describes a configuration for forming the sub beam for reliably creating a blind spot of sensitivity in the target region while maintaining high sensitivity to produce the advantageous effect of sharpening of angle of the main beam, even in the case of an ultrasonic diagnostic apparatus.

Figure 2A:
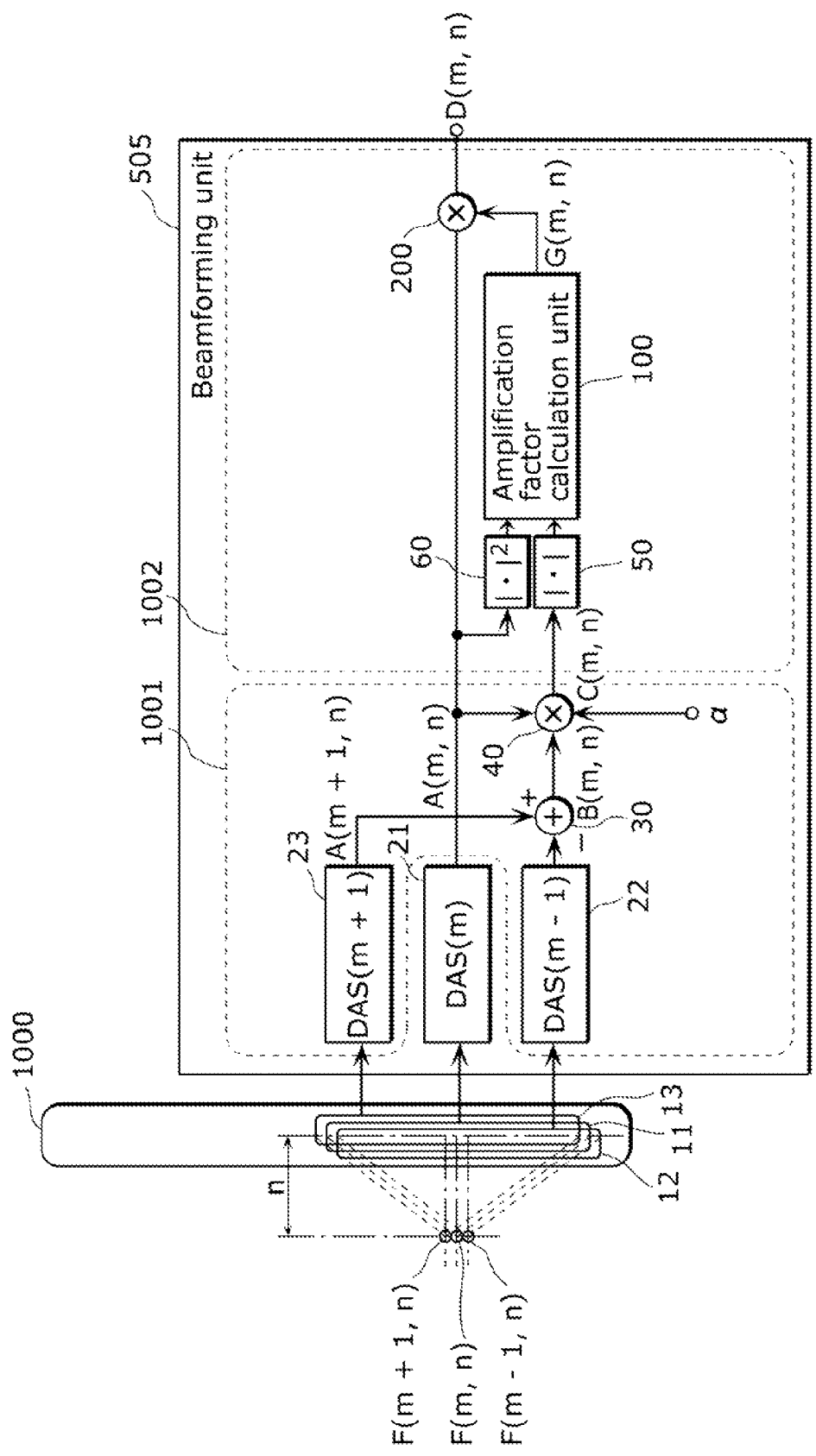
FIG. 2A is a diagram showing a first example of a beamforming method according to Embodiment 1.

FIG. 2A shows a configuration of the beamforming unit 505 according to this embodiment.

The beamforming unit 505 includes: a first DAS unit 21, a second DAS unit 22, a third DAS unit 23, a first subtraction unit 30, a first multiplication unit 40, a first absolute value arithmetic unit 50, a first power arithmetic unit 60, a first amplification factor calculation unit 100, and a second multiplication unit 200. Furthermore, the beamforming unit 505 receives a signal from a receiving unit 1000.

The receiving unit 1000 includes a plurality of receiving elements which receive ultrasound waves reflected off a specimen. Each of the receiving elements receives ultrasound waves, and amplifies signals which correspond to the received ultrasound waves, and convert (analog-to-digital (AD) conversion) the signals into digital signals, and thus generates a receiving echo signal. In other words, the receiving unit 1000 corresponds to the probe unit 501, the T/R switch unit 502, and the AFE unit 504 shown in FIG. 1.

Among the receiving elements included in the receiving unit 1000, a portion is assumed to be a first receiving element array 11, a portion different from the first receiving element array 11 is assumed to be a second receiving element array 12, and a portion different from both of the first receiving element array 11 and the second receiving element array 12 is assumed to be a third receiving element array 13.

The first DAS unit 21 performs delay processing on an output signal of each of the elements included in the first receiving element array 11, and performs a delay and sum operation using, as a target region (focal point), a position on line m at depth n. Here, the depth n indicates, assuming that the center of the first receiving element array 11 is the origin, a distance in a direction toward the specimen (i.e., a depth direction of the specimen) from the receiving unit 1000. Furthermore, the m is a value which indicates a distance in a direction along the first receiving element array 11 (arrangement direction of the receiving elements) assuming that the center of the first receiving element array 11 is the origin. To express the distance, the interval between the receiving elements is used as a unit.

The second DAS unit 22 performs delay processing on an output signal of each of the elements included in the second receiving element array 12, and performs a delay and sum operation using, as a target region, a position on line (m−1) at depth n.

The third DAS unit 23 performs delay processing of a signal output from each of the elements included in the third receiving element array 13, and performs a delay and sum operation using, as a target region, a position on line (m+1) at depth n.

The first subtraction unit 30 performs subtraction processing of an output signal of the second DAS unit 22 and an output signal of the third DAS unit 23.

The first multiplication unit 40 multiplies an output signal of the first DAS unit 21 by an output signal of the first subtraction unit 30 multiplied by a constant a.

The first absolute value arithmetic unit 50 calculates an absolute value of an output signal of the first multiplication unit 40.

The first power arithmetic unit 60 calculates the square of the absolute value of an output signal of the first DAS unit 21.

The first amplification factor calculation unit 100 calculates an amplification factor G(m, n), using as inputs, an output signal of the first absolute value arithmetic unit 50 and an output signal of the first power arithmetic unit 60.

The second multiplication unit 200 multiplies an output signal A(m, n) of the first DAS unit 21 by the amplification factor G(m, n) calculated by the first amplification factor calculation unit 100. An output signal D(m, n) of the second multiplication unit 200 is an output of the beamforming unit 505.

Note that, the first DAS unit 21 corresponds to a main beam generation unit. The second DAS unit 22, the third DAS unit 23, the first subtraction unit 30, and the first multiplication unit 40 correspond to a sub beam generation unit 1001. The first absolute value arithmetic unit 50, the first power arithmetic unit 60, the first amplification factor calculation unit 100, and the second multiplication unit 200 corresponds to a narrow beam generation unit 1002.

Operations performed by the beamforming unit 505 having the above configuration shall be described.

Figure 2B:
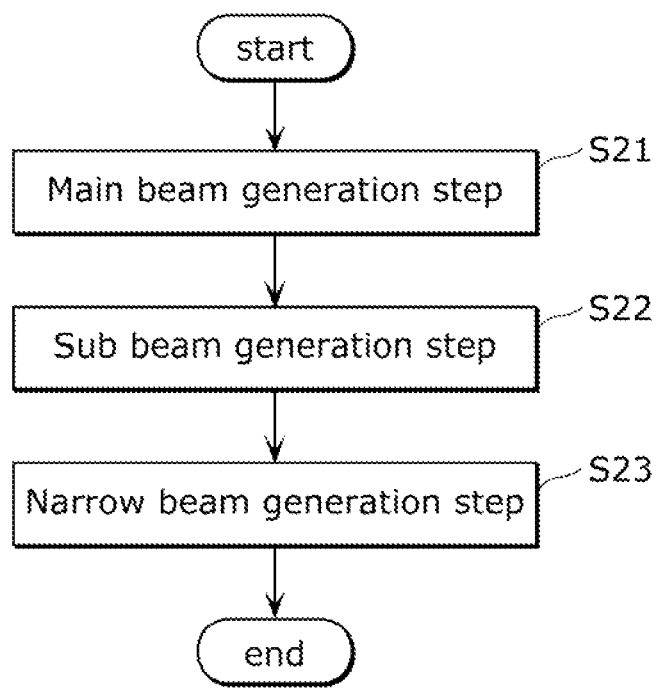
FIG. 2B is a flowchart of the beamforming method according to Embodiment 1.

FIG. 2B is a flowchart of a beamforming method according to this embodiment.

First, the main beam generation unit performs a delay and sum operation on receiving echo signals obtained from the receiving elements, using, as a focal point, a first region of the specimen (a main beam generation step, Step S21).

Next, the sub beam generation unit generates, from the receiving echo signals, a sub beam signal which, compared to the main beam signal, has a low sensitivity to an ultrasound signal reflected off the first region (a sub beam generation step, Step S22). Here, the sub beam generation unit generates the sub beam signal using a differential signal that is a difference between two beam signals each of which is generated by performing a delay and sum operation on the receiving echo signals, using, as a focal point, a corresponding one of two regions of the subject which are different from the first region and are different from each other.

Next, the narrow beam generation unit calculates a coefficient which is determined based on the main beam signal and the sub beam signal, and is for narrowing the angle of the main beam signal, and generates a narrow beam signal by multiplying the main beam signal by the coefficient (a narrow beam generation step, Step S23).

The following describes operations performed by the beamforming unit 505 in more detail.

Note that, n represents a longitudinal direction of an image observed by the ultrasonic diagnostic apparatus (i.e., a depth direction of an observation target) and m represents a line (a line which finally contributes toward forming an image) in a lateral direction (arrangement direction of the receiving elements) of an image observed by the ultrasound diagnostic apparatus.

FIG. 3 is a diagram showing a positional relationship between a receiving unit and the receiving element array, according to Embodiment 1. More specifically, FIG. 3 shows relationships between (i) the receiving unit 1000 including a plurality of receiving elements which receive signals and (ii) the first receiving element array 11, the second receiving element array 12, and the third receiving element array 13 each of which is a set of elements (an example in which the aperture size is 64) which is preset for digital signal sequences obtained from the receiving unit 1000.

(a) in FIG. 3 shows an example of the receiving unit 1000 in which a first receiving element u1 to a 256th receiving element u256 are arranged. (b) in FIG. 3 shows that the second receiving element array 12 is made up of a set of receiving elements which are the first receiving element u1 to a 64th receiving element u64. With the second receiving element array 12, a delay-and-sum output A(m−1, n) of line (m−1) is obtained. (c) in FIG. 3 shows that the first receiving element array 11 is made up of a set of receiving elements which are a second receiving element u2 to a 65th receiving element u65. With the first receiving element array 11, a delay-and-sum output (main beam) A(m, n) of a line m is obtained. (d) in FIG. 3 shows that the third receiving element array 13 is made up of a set of receiving elements which are a third receiving element u3 to a 66th receiving element u66. With the third receiving element array 13, a delay-and-sum output A(m+1, n) of line (m+1) is obtained. In this manner, it is indicated that the second receiving element array 12 and the third receiving element array 13 use sets of elements obtained by shifting, relative to the receiving element array 11, one element in either direction in which the elements are arranged. Furthermore, the combination that includes (b) in FIG. 3 to (d) in FIG. 3 is for the case in which a beamformer result for the line m is obtained. The transmission and reception are repeated by increasing m one by one, and data is accumulated line by line. Thus, data for all the lines is obtained and an ultrasound diagnostic image is generated.

Figure 4:
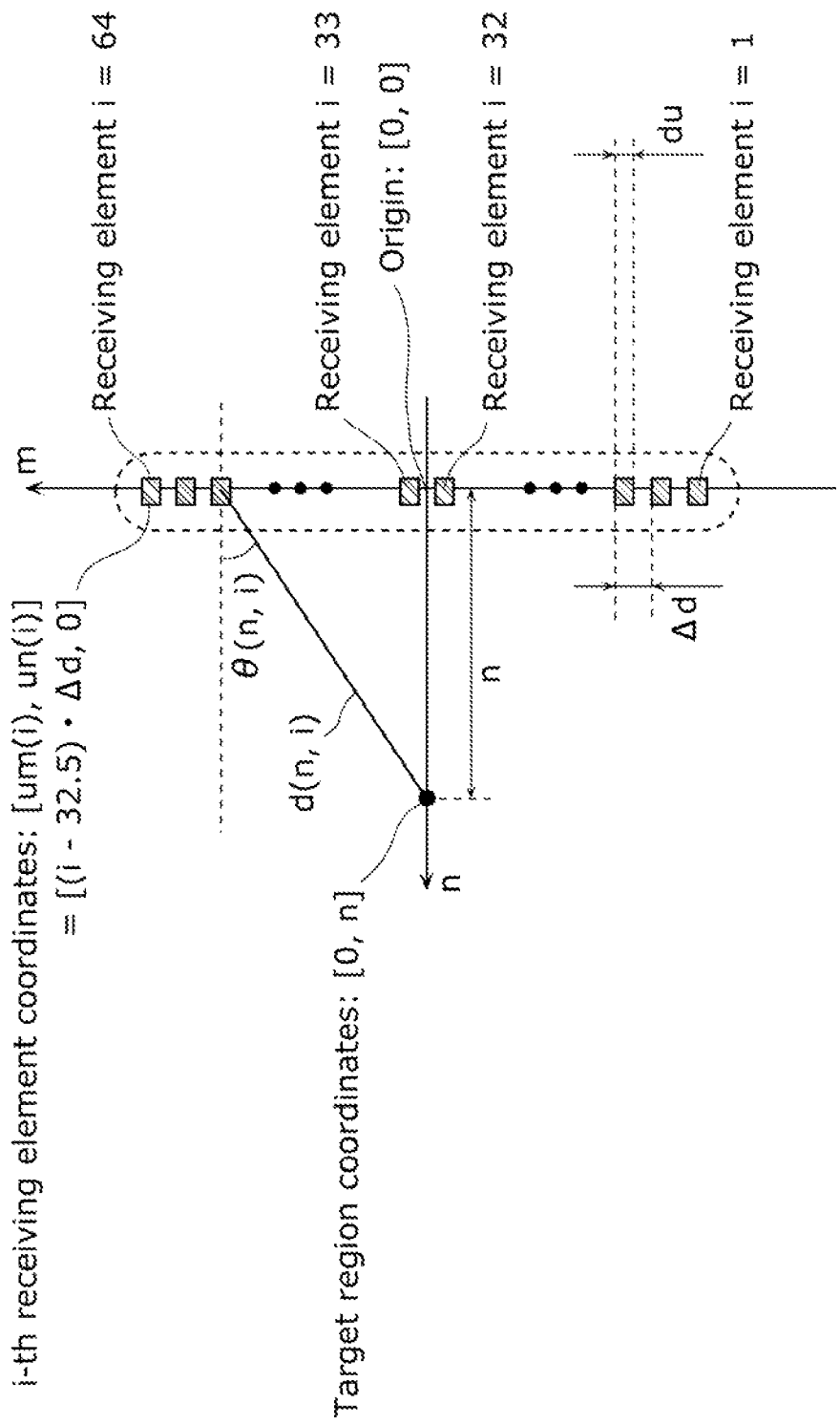
FIG. 4 is a diagram showing a positional relationship between the receiving element and a target region according to Embodiment 1.

FIG. 4 indicates an example of positional relationship between each element of the receiving element array and the target region. The following describes (Expression 1) to (Expression 5) with reference to the positional relationship.

Here, a beam pattern (also called a beam profile) indicates a characteristic of a sensitivity level on line m at depth n. A graph of a characteristic of the beam pattern in the following is considered based on the following delay-and-sum output signal A(k, n). In the following description, a signal A(m, n) means a delay-and-sum output signal obtained from a receiving element array which corresponds to the line m. Furthermore, A(k, n) represents a beam pattern of a delay-and-sum output obtained from the receiving element array which corresponds to the line m, and thus indicates a signal component for coordinates (k, n) assuming that the center of the receiving element array is the origin (0, 0).

Figure 5:
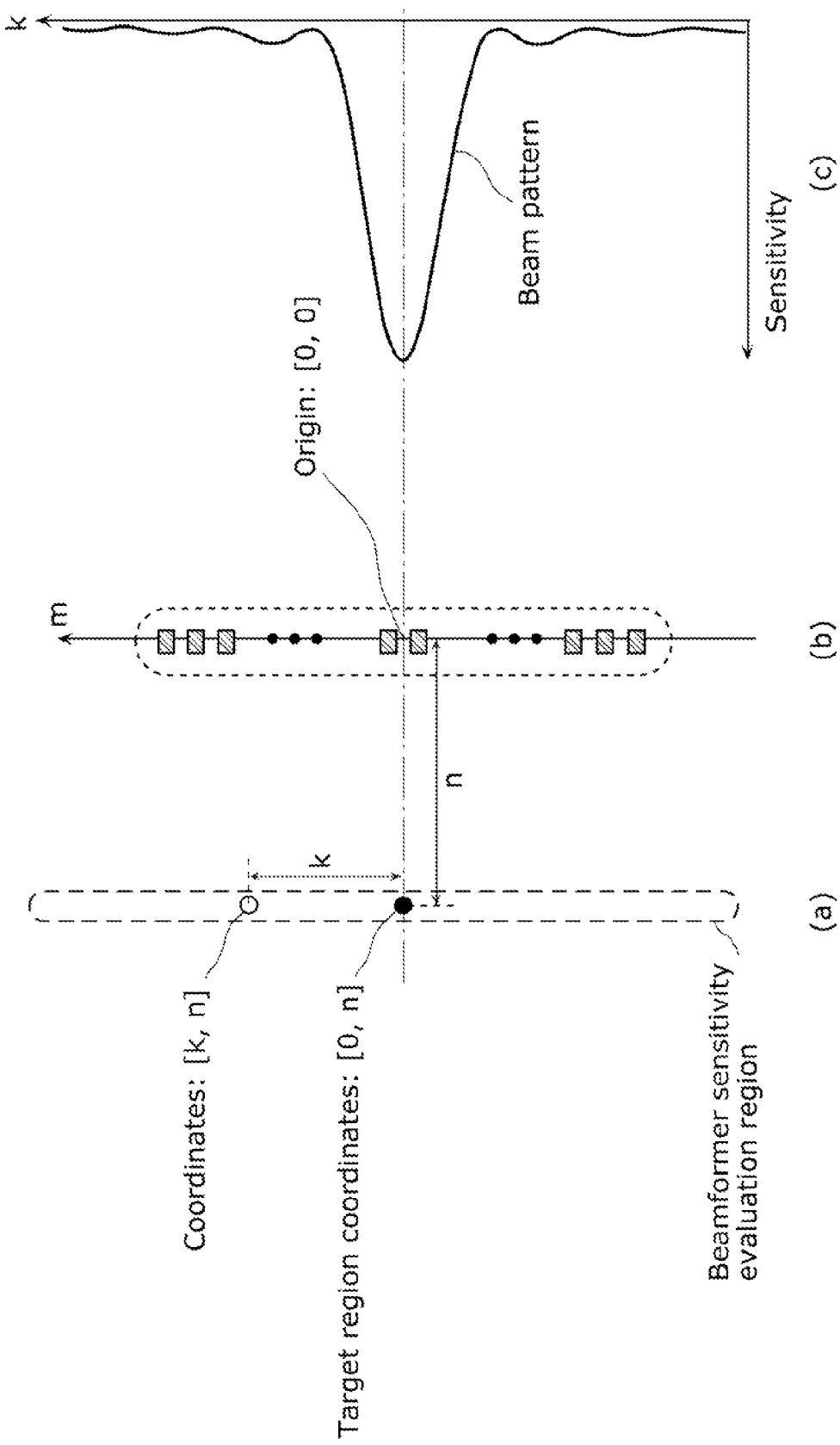
FIG. 5 is a conceptual diagram showing a relationship between a sensitivity evaluation region and receiving sensitivity of the sensitivity evaluation region.

FIG. 5 is a conceptual diagram showing a relationship between a sensitivity evaluation region and a receiving sensitivity of the sensitivity evaluation region. (a) in FIG. 5 shows the sensitivity evaluation region. (b) in FIG. 5 shows the receiving element array. (c) in FIG. 5 shows a beam pattern.

Assuming that coordinates of a line k at depth n is (k, n), and coordinates of i-th receiving element is (um(i), un(i)), a distance d(k, n, i) from the target region at depth n to each receiving element is represented by (Expression 1).

[Math. 1]

$$d(k,n,i) = \mathrm{sqrt}\{(k-um(i))^2 + (n-un(i))^2\} \quad \text{(Expression 1)}$$

When the center of the receiving element array is set to the origin (0, 0) as shown in FIG. 4, the coordinates of the target region are (0, n), and the coordinates of the i-th receiving element are (um(i), un(i))=((i−32.5)·Δd, 0).

Here, Δd represents an element interval, and Δd=0.3 mm.

The delay-and-sum operation is a computation in which phases of ultrasound waves propagated from the target region (0, n) to the elements are matched, and addition is performed in a manner to intensify the ultrasound waves propagated to the elements. The phases of the ultrasound waves are matched by making a correction to delay, by the time corresponding to a distance d(k, n, i) to each receiving element, the ultrasound waves transmitted from the target region at depth n. The time delay is represented by (Expression 2).

[Math. 2]

$$\tau(n, i) = \frac{d0 - d(0, n, i)}{c} \quad \text{(Expression 2)}$$

Here, d0 denotes a reference distance. It is sufficient that d0 be greater than the distance from the target region to a receiving element (i=1) or a receiving element (i=64), which are located farthest from the target region, so that the value of τ(n, i) is not negative. In other words, d0≥d(0, n, 1) is satisfied. c denotes a speed of sound, and is assumed to be 1530 m/sec which is an average speed of sound in a body.

The beam pattern A(k, n) of the delay-and-sum output is represented by (Expression 3) to (Expression 6) where time necessary to travel a distance to the i-th receiving element from coordinates (k, n) is denoted by d(k, n, i)/c, time delay processed by a subsequent-stage delay unit of each element is denoted by τ(n, i), directivity of the receiving element for an angle θ(k, n, i), which is an angle of an i-th receiving element with respect to coordinates (k, n), is denoted by UD(θ(k, n, i)), an amount of signal attenuation over the distance d(k, n, i) to the i-th receiving element from the coordinates (k, n) is denote by ATT(d(k, n, i)), and a width of the receiving element is denote by du.

[Math. 3]

$$A(k, n) = \sum_{i=1}^{64} (\exp(-j2\pi f d(k, n, i)/c) \cdot \quad \text{(Expression 3)}$$

$$\exp(-j2\pi f \tau(n, i)) \cdot UD(\theta(k, n, i)) \cdot ATT(d(k, n, i)))$$

[Math. 4]

$$ATT(d(k, n, i)) = 10^{-0.05 f \cdot d(k,n,i)/20} \quad \text{(Expression 4)}$$

[Math. 5]

$$\theta(k, n, i) = \sin^{-1}\left(\frac{um(i)}{d(m, n, i)}\right) \quad \text{(Expression 5)}$$

[Math. 6]

$$UD(\theta(k, n, i)) = \int_{-1/2}^{1/2} \exp\left(-j2\pi f \frac{du \cdot x \cdot \sin(\theta(k, n, i))}{c}\right) dx \quad \text{(Expression 6)}$$

A main beam generation unit includes the first receiving element array 11, and the first DAS unit 21. Here, it is assumed that the target region of the main beam signal A(m, n), which is a delay-and-sum output signal, is F(m, n) shown in FIG. 2A that is a position on line m at depth n.

Next, the sub beam generation unit 1001 is described. An ideal beam pattern of the sub beam at least, compared to the main beam signal A(m, n), includes a blind spot of sensitivity (a state in which sensitivity is sufficiently low) to the target region F(m, n), and it is preferable that the sub beam has high resemblance to the main beam in a region (a region in which low sensitivity is preferred) which is away from the target region F(m, n).

The first subtraction unit 30 obtains, as the sub beam, a signal B(m, n) which is obtained as a difference between a delay-and-sum output signal A(m−1, n) having a focal point at a position F(m−1, n) and a delay-and-sum output signal A(m+1, n) having a focal point at a position F(m+1, n). Here, the delay-and-sum output signal A(m−1, n) is a delay-and-sum signal obtained by the second receiving element array 12 and the second DAS unit 22. Furthermore, the delay-and-sum output signal A(m+1, n) is a delay-and-sum signal obtained by the third receiving element array 13 and the third DAS unit 23.

[Math. 7]

$$B(m,n)=A(m-1,n)-A(m+1,n) \quad \text{(Expression 7)}$$

Figure 6:
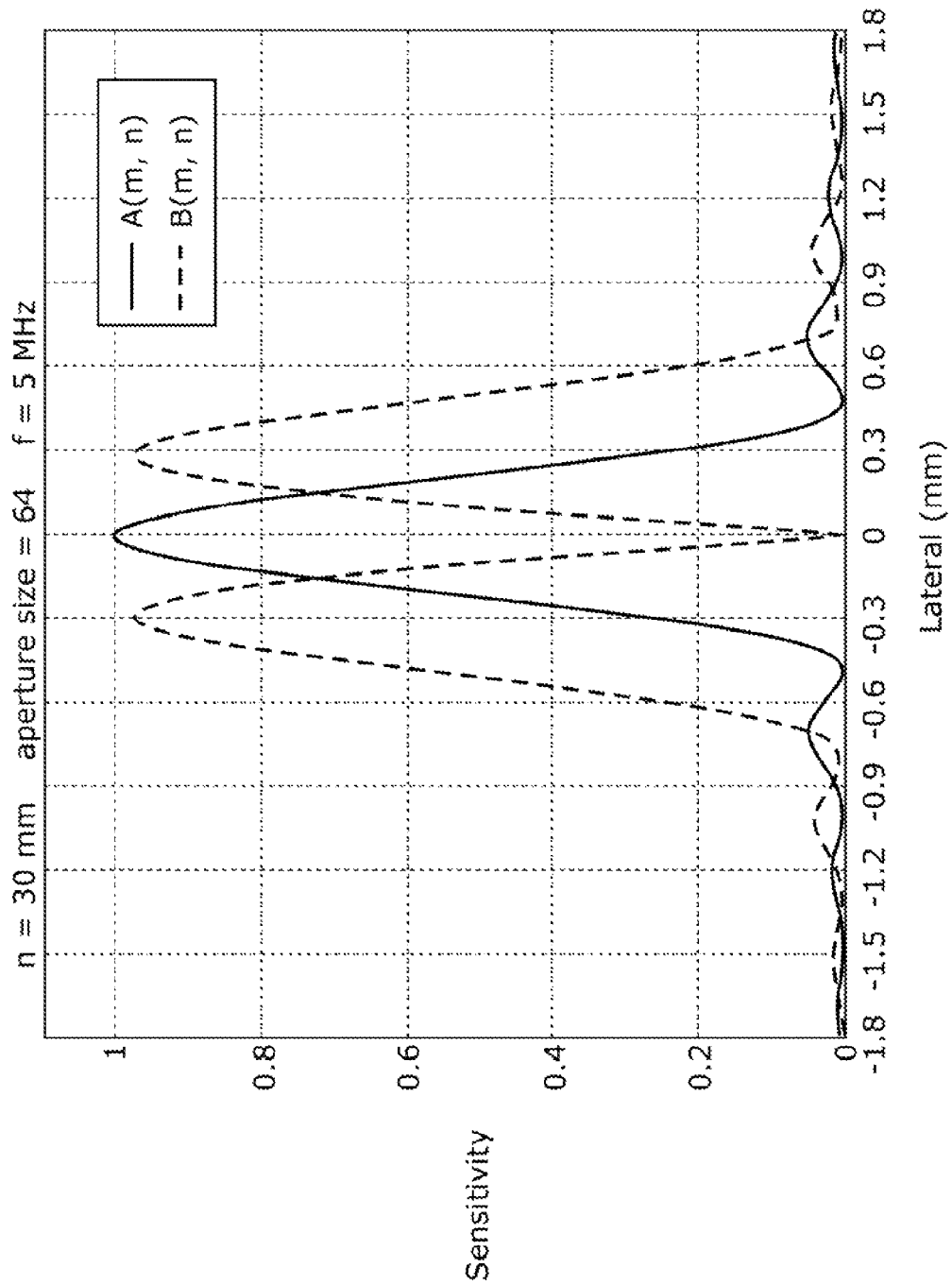
FIG. 6 is diagram showing a first example of beam patterns of a main beam signal A(m, n) and signals B(m, n) according to Embodiment 1.

FIG. 6 is a diagram showing a first example of beam patterns of (i) the main beam signal A(m, n) calculated according to (Expression 1) to (Expression 6) and (ii) the above-described signal B(m, n). In FIG. 6, the horizontal axis represents a position (mm) in the arrangement direction of elements, and the center position of the main beam is assumed to be 0 mm. The vertical axis represents a value of sensitivity of the beam. Note that, the calculations of the beam patterns are performed under conditions of the depth n=30 mm, the aperture size L=64 elements, element intervals Δd=0.3 mm, and frequency f=5 MHz.

The results of the delay and sum operations on line (m−1) and line (m+1), which are symmetrical with respect to the line m of the main beam, are regarded as new signals, and the signal B(m, n) is obtained by performing a subtraction on the new signals. The two signals having focal points at positions which are symmetrical relative to the target region of the main beam are subtracted. Thus, levels and phases of the two signals match each other at the focal point of the main beam, and the blind spot of sensitivity is created. Furthermore, the two signals are signals after the delay-and-sum output, and thus has higher resistance to a variation, a change in a speed of sound, or the like, which makes it possible to reliably produce a signal cancellation effect in the target region. Furthermore, since the subtraction is performed on the beams which form focal points at two different positions, it is possible to produce the advantageous effect of reducing reduction in sensitivity in a portion other than the blind spot of sensitivity. With this, it is possible to ensure robustness and solve the problem of reduction in sensitivity when the subtraction-type beamformer is applied to the ultrasonic diagnostic apparatus.

However, as shown in FIG. 6, since the signal B(m, n) is obtained based on the results of the delay and sum operation in which focal points are positioned in two different regions, which are the region of the line (m−1) and the region of the line (m+1), the positions having greatest sensitivities in the beam patterns appear at positions of ±0.3 mm that are the same as the pitch of elements (an interval between the lines). For the sub beam, the position having the greatest sensitivity be closer to 0 mm is necessary to sharpen the angle of the beam.

In view of this, to narrow the width between the two positions, which indicate the highest sensitivity, of the signals B(m, n), the following processing is further performed.

[Math. 8]

$$C(m,n)=\alpha \cdot A(m,n) \cdot B(m,n) \quad \text{(Expression 8)}$$

In other words, according to (Expression 8), the first multiplication unit 40 obtains an output signal C(m, n) by multiplying the output signal B(m, n) of the first subtraction unit 30 by the output signal A(m, n) of the first DAS unit 21 multiplied by the constant a.

Figure 7:
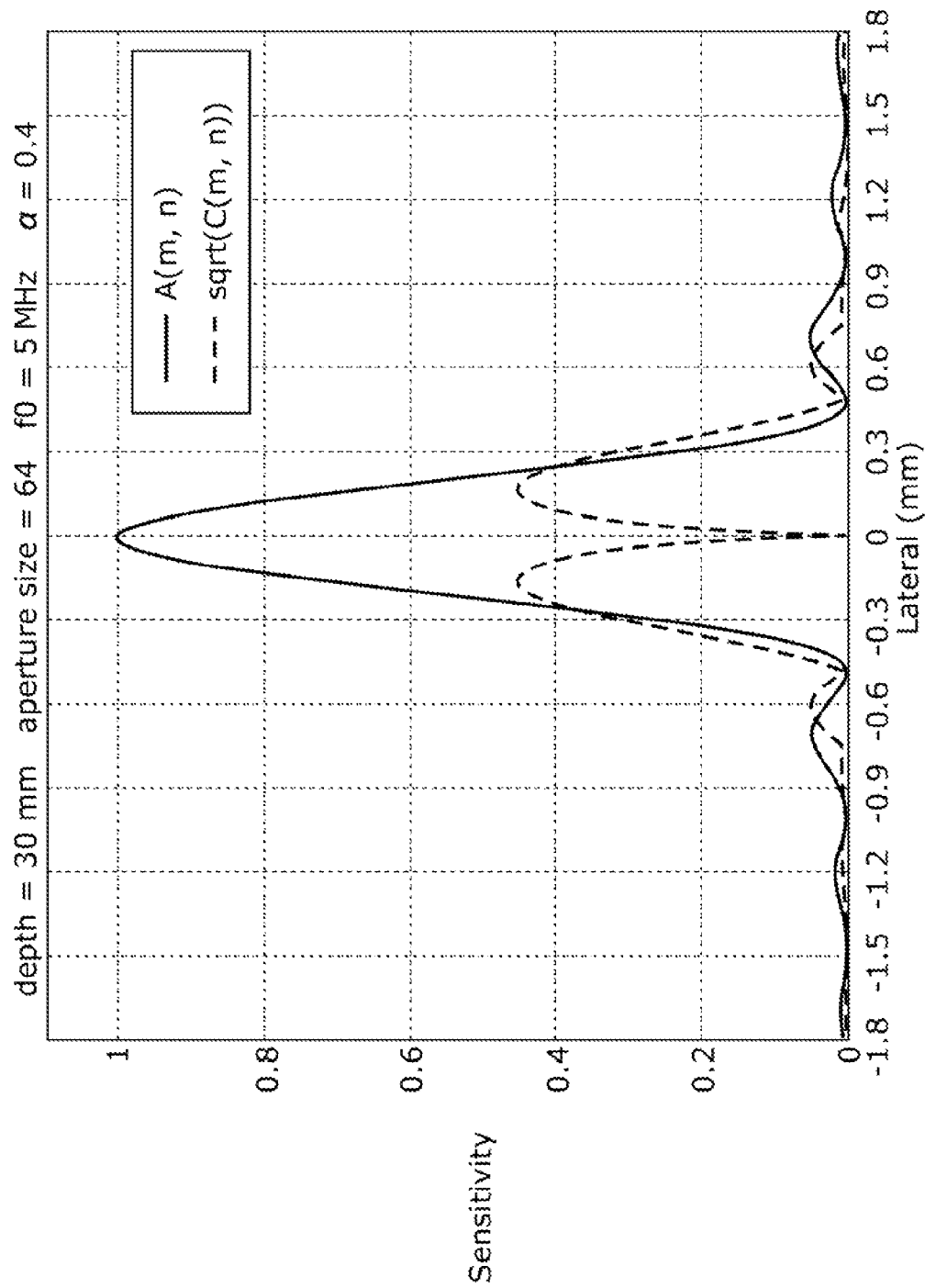
FIG. 7 is a diagram showing beam patterns of a main beam output A(m, n) of a first delay and sum (DAS) unit and a sub beam output C(m, n) of a first multiplication unit, according to Embodiment 1.

FIG. 7 shows beam patterns of the main beam signal A(m, n) and the output signal C(m, n) of the first multiplication unit 40.

As shown in FIG. 7, by multiplying A(m, n) having the greatest sensitivity at the position of 0 mm by B(m, n) having the greatest sensitivity at the positions of ±0.3 mm, the greatest sensitivity position of the output signal C(m, n) can be set to a position between A(m, n) and B(m, n). As a result, the greatest sensitivity positions appear at approximately ±0.15 mm, and thus narrowing of the width between the two greatest sensitivity positions is achieved. Furthermore, with the adjustment of a sensitivity level by constant a (a=0.4 in FIG. 7), a beam pattern of a sub beam C(m, n) which is in high agreement with the beam pattern of the main beam signal A(m, n) is obtained.

The first absolute value arithmetic unit 50 calculates an absolute value of an output signal C(m, n) of the first multiplication unit 40. Furthermore, the first power arithmetic unit 60 calculates and outputs the square of the output signal A(m, n) of the first DAS unit 21. The signal C(m, n) is obtained by multiplying signal A(m, n) by signal B(m, n), and thus the dimension of the signal C(m, n) is power. Thus, the first absolute value arithmetic unit 50 calculates the absolute value of the signal C(m, n) and the first power arithmetic unit 60 calculates the power of signal A(m, n), and thus the dimensions of the signals are matched with each other.

The first amplification factor calculation unit 100 calculates the amplification factor G, using as inputs, the output signal of the first absolute value arithmetic unit 50 and the output signal of the first power arithmetic unit 60. Here, an example in which the amplification factor is calculated according to a method which reduces a noise component (unwanted component) mixed in a main signal, by using a power spectrum of the main signal and a reference signal (sub signal) as with the commonly known spectrum subtraction method or Wiener filter method. Furthermore, in the spectrum subtraction method or the like, which handles a broadband signal, for an acoustic signal in an audible range, it is general that a power spectrum is obtained and subtracted for each frequency component. However, in the case of an ultrasonic diagnostic apparatus, a signal to be handled is in a relatively narrow band, and thus processing in a single band is used instead.

The first amplification factor calculation unit 100 can obtain, for example, as a multiplier, an amplification factor G(m, n) which reduces a noise component by using a signal power, according to the following expression.

[Math. 9]

$$G(m, n) = \frac{|A(m, n)|^2 - \alpha \cdot |C(m, n)|}{|A(m, n)|^2} \quad \text{(Expression 9)}$$

Note that, G(m, n)=β when G(m, n)<β. β is a constant for limiting an attenuation amount, and 0≤β<1 is satisfied.

A numerator of (Expression 9) is a power of the resulting signal after subtracting the sub beam signal C(m, n) from the main beam signal A(m, n). More specifically, with the operation of power subtraction, a broken line (C(m, n)) is subtracted from a solid line (A(m, n)) in FIG. 7, and thus it is possible to reduce the sensitivity outside the range of ±0.15 mm. As a result, the first amplification factor calculation unit 100 obtains a power of target signal which has a narrower angle.

Furthermore, the right-hand side of (Expression 9) includes a power of input signal in the denominator and includes the power of target signal in the numerator. The numerator represents a method of calculating gain for reduction based on the Wiener filter method. Thus, the amplification factor G(m, n) is an attenuation amount for removing a component of the sub beam signal C(m, n) from the main beam signal A(m, n). The second multiplication unit 200 outputs an output signal D(m, n) of the beamforming unit 505 by multiplying the main beam signal A(m, n) by the amplification factor G(m, n).

[Math. 10]

$$D(m,n)=A(m,n)\cdot G(m,n) \qquad \text{(Expression 10)}$$

Figure 8:
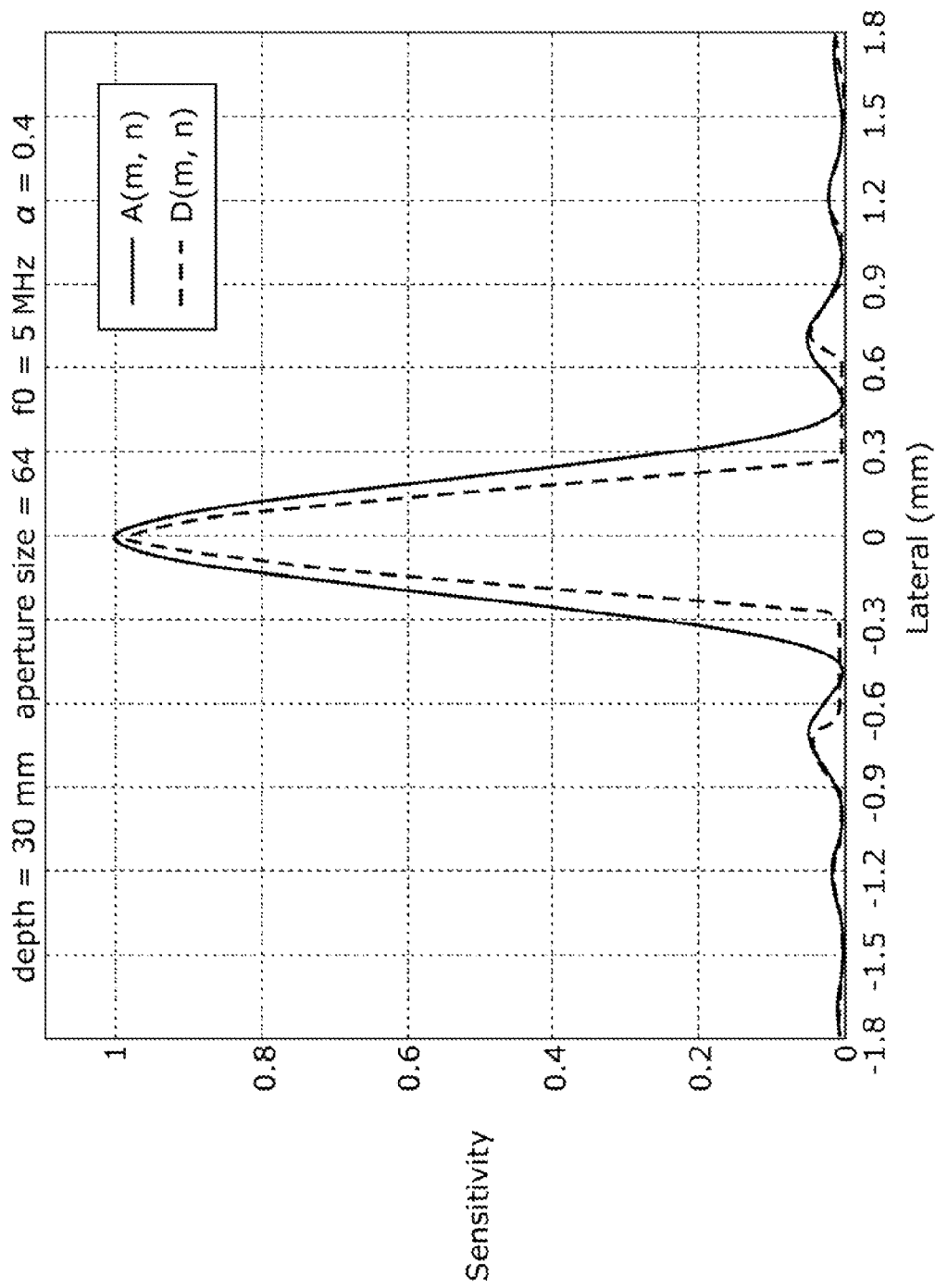
FIG. 8 is a diagram showing beam patterns of the main beam output A(m, n) of the first DAS unit and a beamformer output D(m, n) of a second multiplication unit, according to Embodiment 1.

FIG. 8 is a diagram showing a main beam signal A(m, n) from a first DAS unit and a beam signal D(m, n) which is obtained by narrowing the angle of the main beam signal.

In this manner, a narrower beam signal (having a narrower angle) compared to the main beam signal which is obtained based on the conventional delay and sum method can be realized. As a result, it is possible to improve the resolution and quality of an image by generating the image using a signal which has been beamformed using a beamforming method according to this embodiment.

Note that, in Embodiment 1 it has been described that the ultrasonic diagnostic apparatus 1 outputs a beamformer output signal D(m, n) of the line m. Here, for the transmission signal which is transmitted to the line m, the first DAS unit 21, the second DAS unit 22, and the third DAS unit 23, may be simultaneously operated in parallel or may be operated by time-sharing of one DAS unit (i.e., a DAS unit may be shared). More specifically, processing of a subsequent-stage of a DAS unit may be performed after using (i) a DAS unit output on the line m for a transmission signal transmitted to the line m at reception time t2 as the output signal of the first DAS unit 21, (ii) a DAS unit output on the line (m−1) for a transmission signal transmitted to the line (m−1) at reception time t1 as the output signal of the second DAS unit 22, and (iii) a DAS unit output on the line (m+1) for a transmission signal transmitted to the line (m+1) at reception time t3 as the output signal of the third DAS unit 23.

Note that, the relationship between (i) a target region F(m, n) set by the first DAS unit 21 and (ii) two beam focal points F(m−1, n) and F(m+1, n) of the second DAS unit 22 and the third DAS unit 23 for generating the sub beams may be a positional relationship with which a signal is cancelled (i.e., a blind spot of sensitivity is created) in the target region F(m, n) when subtraction is performed on signals from the second DAS unit 22 and the third DAS unit 23. More specifically, two beam focal points F(m−Δ, n) and F(m+Δ, n) of the second DAS unit 22 and the third DAS unit 23 for generating the sub beams, may be in relationship to be symmetric around the line which connects the target region F(m, n) of a main beam and the center of the receiving element array. Stated differently, it is sufficient that the two beam focal points F(m−Δ, n) and F(m+Δ, n) of the second DAS unit 22 and the third DAS unit 23 are at equal distances from the target region F(m, n) of the main beam and from the center of the receiving element array. An example in which Δ is 2 is shown in FIG. 9 and FIG. 10.

Figure 9:
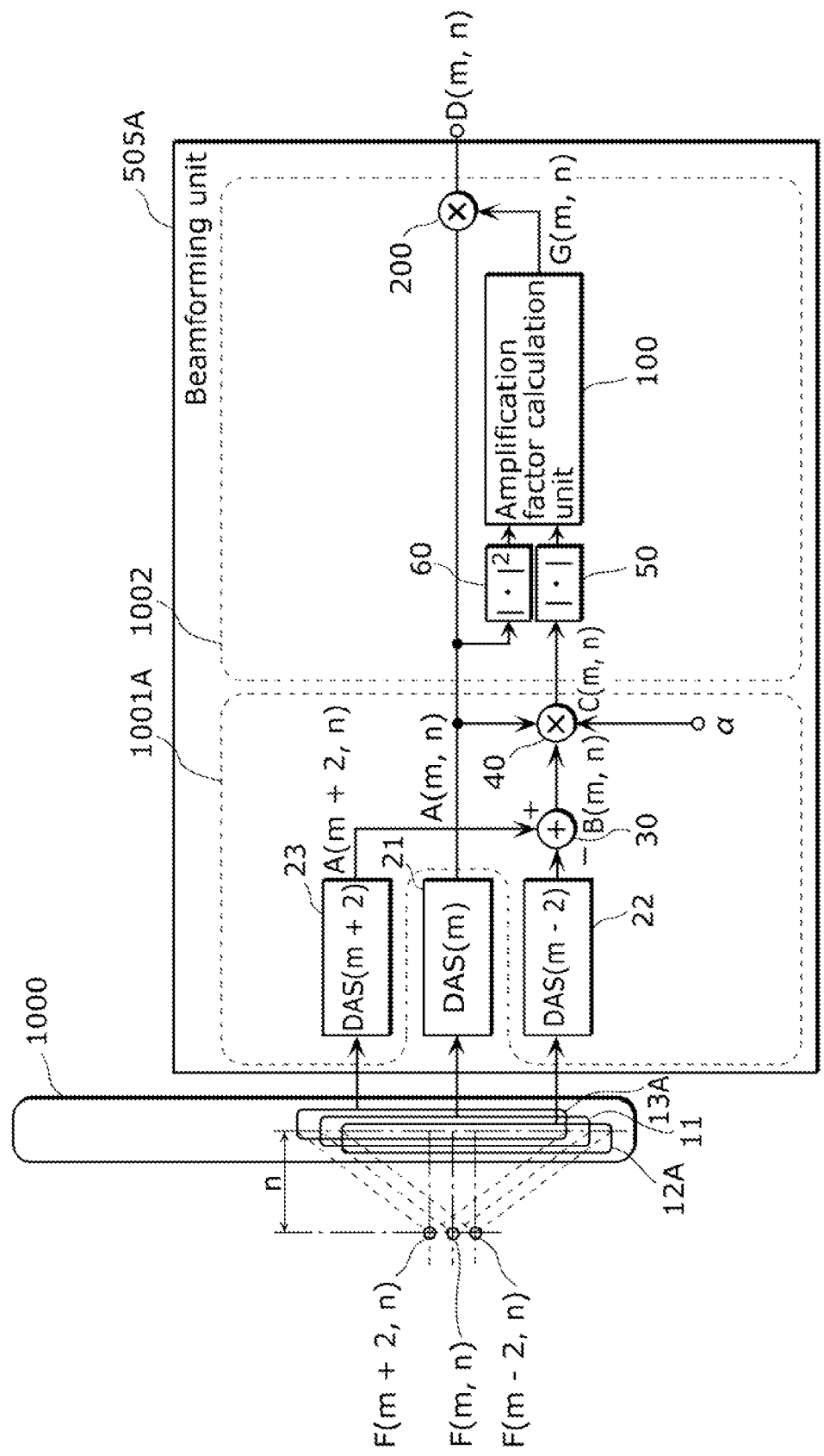
FIG. 9 is a diagram showing a second example of a beamforming method according to Embodiment 1.

FIG. 9 is a diagram which shows a second example of a beamforming method according to this embodiment. A second receiving element array 12A is a set of elements obtained by shifting two elements relative to the first receiving element array 11. Furthermore, a third receiving element array 13A is a set of elements obtained by shifting, in a direction opposite to the second receiving element array 12A, two elements relative to the first receiving element array 11.

In a sub beam generation unit 1001A, the second DAS unit 22 performs a delay and sum operation on a signal from the second receiving element array 12A. Furthermore, the third DAS unit 23 performs a delay and sum operation on a signal from the third receiving element array 13A.

Figure 10:
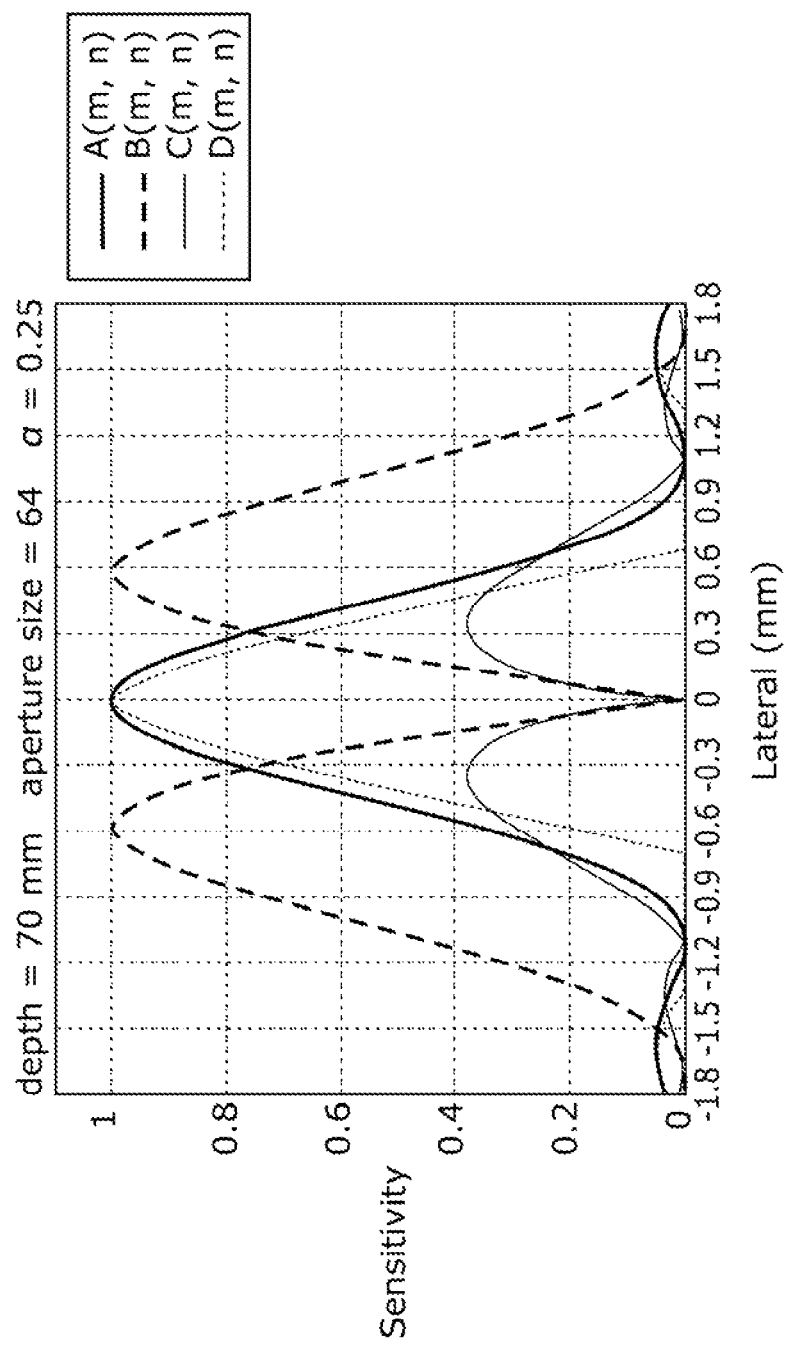
FIG. 10 is a diagram showing a second example of beam patterns of the signals A(m, n) to D(m, n) according to Embodiment 1.

FIG. 10 is a diagram showing a second example of beam patterns of signals A(m, n) to D(m, n) according to this embodiment. Compared with the beam patterns shown in FIG. 6, the beam patterns shown in FIG. 10 are wider by the number of the elements shifted. In this case as well, the ultrasonic diagnostic apparatus 1 can obtain the signal D(m, n) by narrowing the angle of the main beam signal A(m, n) in a similar manner as the above.

Furthermore, regarding the sub beams, even when there is a slight difference in depths n of the two focal points of beams, such as (i) F(m−1, n+Δ) and F(m+1, n+Δ) or (ii) F(m−1, n−Δ) and F(m+1, n−Δ), for the delay and sum operation for generating the sub beams, a blind spot of sensitivity is included in the target region F(m, n) and the advantageous effect of sharpening the angle of the beam can be produced, as long as the above-described line symmetry is maintained. However, Δ is a value smaller than a width of a main lobe beam of the main beam.

As described above, with the beamforming method according to this embodiment, the ultrasonic diagnostic apparatus can narrow the angle of the sensitivity characteristic of a received beam signal. More specifically, with this beamforming method, the angle of the main beam signal obtained from a region of interest of a specimen is narrowed, by using two sub beam signals obtained from regions of the specimen which are different from the region of interest. Here, each of the two sub beam signals includes a signal obtained from the region of interest. Thus, by using a differential signal of the two sub beam signals, an ultrasonic diagnostic apparatus can generate a signal having a blind spot of sensitivity in the region of interest of the main beam signal. Then, the angle of the main beam signal is narrowed by operating on the generated signal and the main beam signal. Thus, with this beamforming method, the ultrasonic diagnostic apparatus can enhance the resolution of an ultrasound diagnostic image to be obtained.

Furthermore, with this beamforming method, the ultrasonic diagnostic apparatus can narrow the angle of the blind spot of sensitivity of the signal generated from the sub beam signals. The angle of the main beam signal can be further narrowed by operating on the signal in which the angle of blind spot of sensitivity has been narrowed and the main beam signal. Thus, with this beamforming method, the ultrasonic diagnostic apparatus can further enhance the resolution of the ultrasound diagnostic image to be obtained.

Furthermore, with this beamforming method, the ultrasonic diagnostic apparatus can adjust the degree of narrowing of angle of the blind spot of sensitivity of the signal generated from the sub beam signals. Thus, with this beamforming method, the ultrasonic diagnostic apparatus can adjust the degree of resolution enhancement of the ultrasound diagnostic image to be obtained.

Furthermore, with this beamforming method, the ultrasonic diagnostic apparatus can generate a signal which has a blind spot of sensitivity in a region of interest of a specimen. The signals obtained by performing delay and sum operation using, as a focal point, each of the two regions have an identical sensitivity at a position corresponding to the region of interest. Thus, the differential signal of these signals has, at a position corresponding to the region of interest, a blind spot of sensitivity where sensitivity is 0. With this, the ultrasonic diagnostic apparatus can narrow the angle of the main beam signal more accurately.

Furthermore, with this beamforming method, the ultrasonic diagnostic apparatus can sequentially generate the main beam signal and the sub beam signal, and, narrow the angle of the main beam signal by using the generated signals.

Embodiment 2

Figure 11:
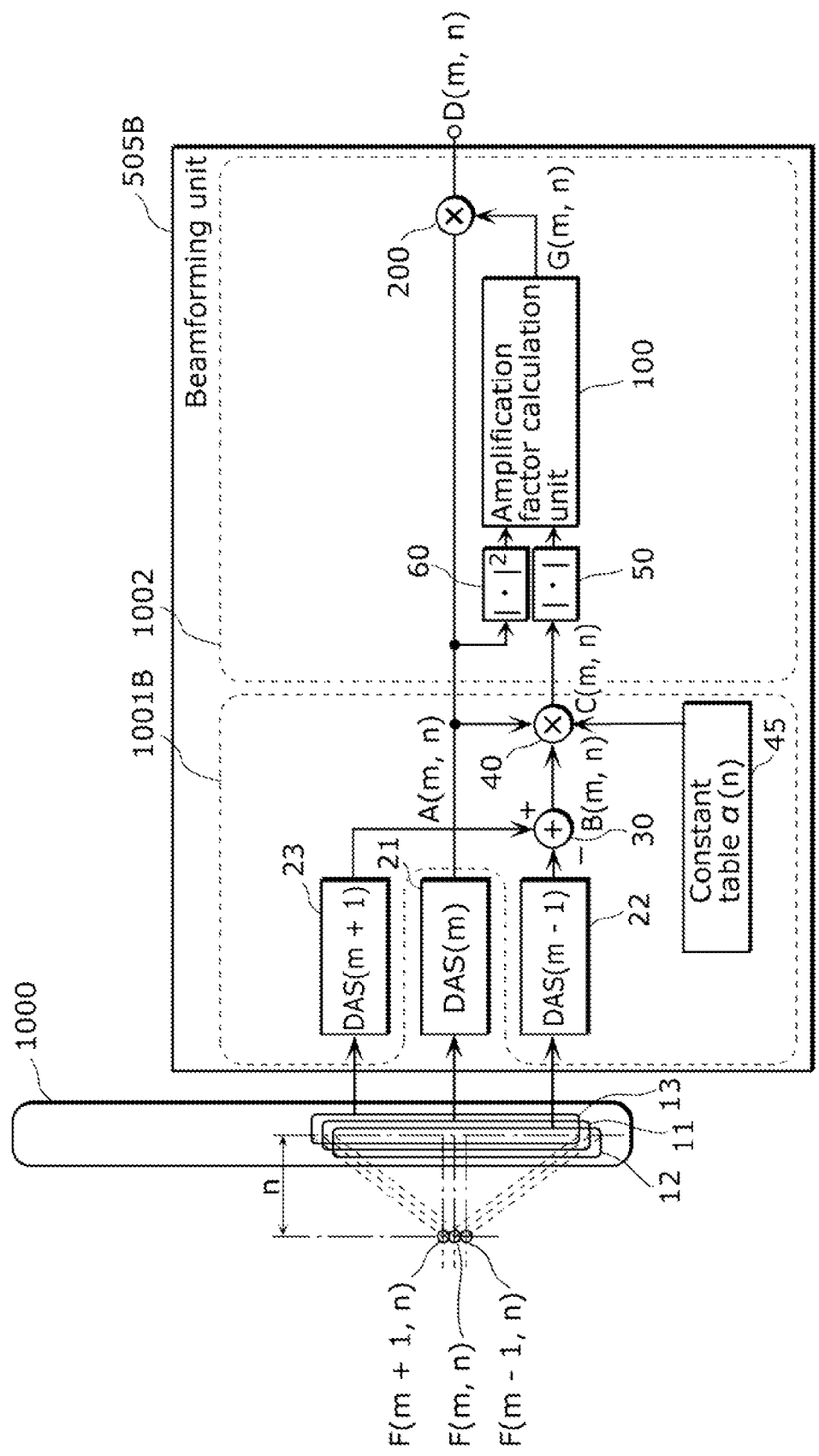
FIG. 11 is a diagram showing an example of a beamforming method according to Embodiment 2.

FIG. 11 is a block diagram of a bear forming unit 505A according to this embodiment.

In FIG. 11, structural elements which are the same as structural elements included in a beamforming unit 505 in FIG. 2A are assigned the same reference signs as those in FIG. 2A and their descriptions shall be omitted.

Different from the beamforming unit 505 in Embodiment 1, a beamforming unit 505B according to this embodiment shown in FIG. 11 includes, instead of a constant a which is one of the inputs of the first multiplication unit 40, a sub beam generation unit 1001B additionally including a constant table 45 which corresponds to a depth n.

Operations performed by the beamforming unit 505B having the above configuration shall be described.

Figure 12:
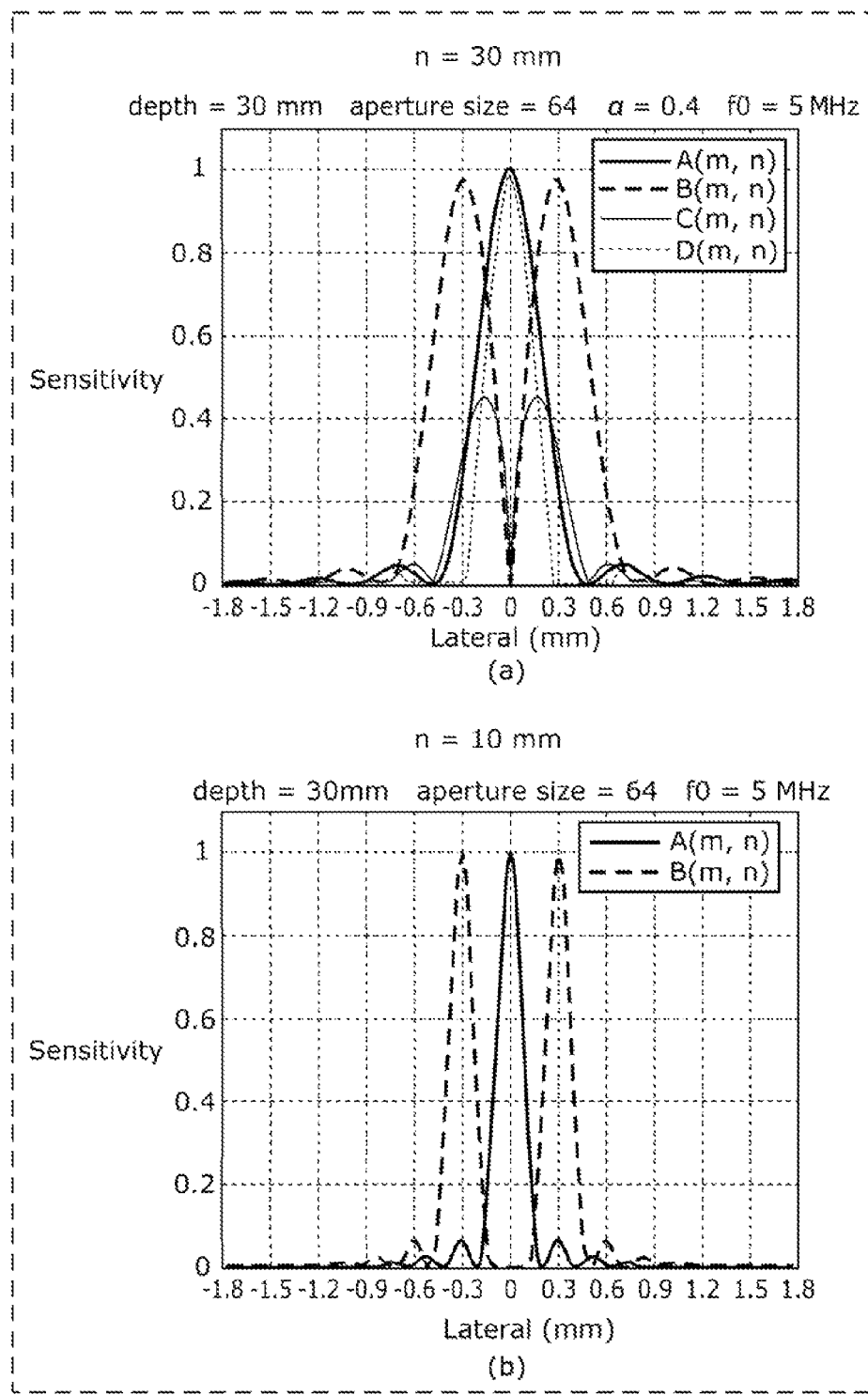
FIG. 12 shows diagrams for comparing beam patterns at different depths n.

FIG. 12 is an example showing beam patterns of two cases in which depths n of focal points are different. (a) in FIG. 12 is an example showing signal A(m, n) to signal D(m, n) of the case in which the depth n=30 mm with conditions the same as the conditions for FIG. 6 to FIG. 8. (b) in FIG. 12 is a beam pattern of the case in which the depth n=10 mm. With respect to the main beam signal A(m, n) output from the first DAS unit 21, a signal B(m, n) output from the first subtraction unit 30 barely overlaps in a portion having a high sensitivity, and a signal C(m, n) obtained by the calculation performed by the first multiplication unit 40 becomes small. Stated differently, for the range in which the depth n is approximately 10 mm, a beam which is sufficiently sharp to allow separation from the adjacent line can be obtained by a delay and sum operation alone, indicating that further sharpening of angle is not particularly beneficial. In this manner, depending on the depth n (a distance from the receiving element array), the beam pattern differs. More specifically, depending on the depth n, the optimal value of the constant a is different. In view of this, the beamforming unit 505B additionally includes the constant table 45 which corresponds to the depth n.

Generally, a focal point at the time of receiving in an ultrasonic diagnostic apparatus is moved based on delay control corresponding to the depth n by using a function called dynamic focusing, and the ultrasonic diagnostic apparatus performs the delay and sum operation while moving the focal point. As shown in FIG. 12, the beam pattern changes corresponding to the depth n of the target region. Thus, it is preferable that the constant a be an optimal value corresponding to the depth. Furthermore, sometimes, another control, such as controlling called a dynamic opening control, which controls duration of opening corresponding to the depth n (the shallower, the shorter the opening duration is) of the target region is used together. This also affects the beam pattern. Thus, the angle of the beam can be sharpened more accurately by preparing beforehand, according to these conditions, a constant table a(n) which is appropriate for a depth n, and controlling a degree of effects made by the sub beam.

Note that, a setting for a level adjustment through a user interface may be made possible to allow a user to arbitrarily provide the constant table 45 for a constant a. For example, the constant a can be adjusted while observing the state on the display unit 507, by allowing details of the constant table 45 to be provided with an operation unit 508 shown in FIG. 1.

Note that, although the above described an example in which the sub beam generation unit 1001B includes a constant table for a, in the case of the method which can determine a in a similar manner as the above, the constant table may be omitted.

As described above, with the beamforming method according to this embodiment, an ultrasonic diagnostic apparatus can adjust the degree of narrowing of angle of a blind spot of sensitivity, based on the depth of the region of interest of a specimen from the surface of the body of the specimen.

Furthermore, with this beamforming method, an ultrasonic diagnostic apparatus can adjust the degree of narrowing of angle of the blind spot of sensitivity, following an operation by a user. A propagation characteristic of ultrasound waves changes due to various factors. Thus, with a fine adjustment of the predetermined constant by a user, an ultrasonic diagnostic apparatus can adjust the degree of narrowing of angle of the blind spot of sensitivity more appropriately.

Embodiment 3

Figure 13:
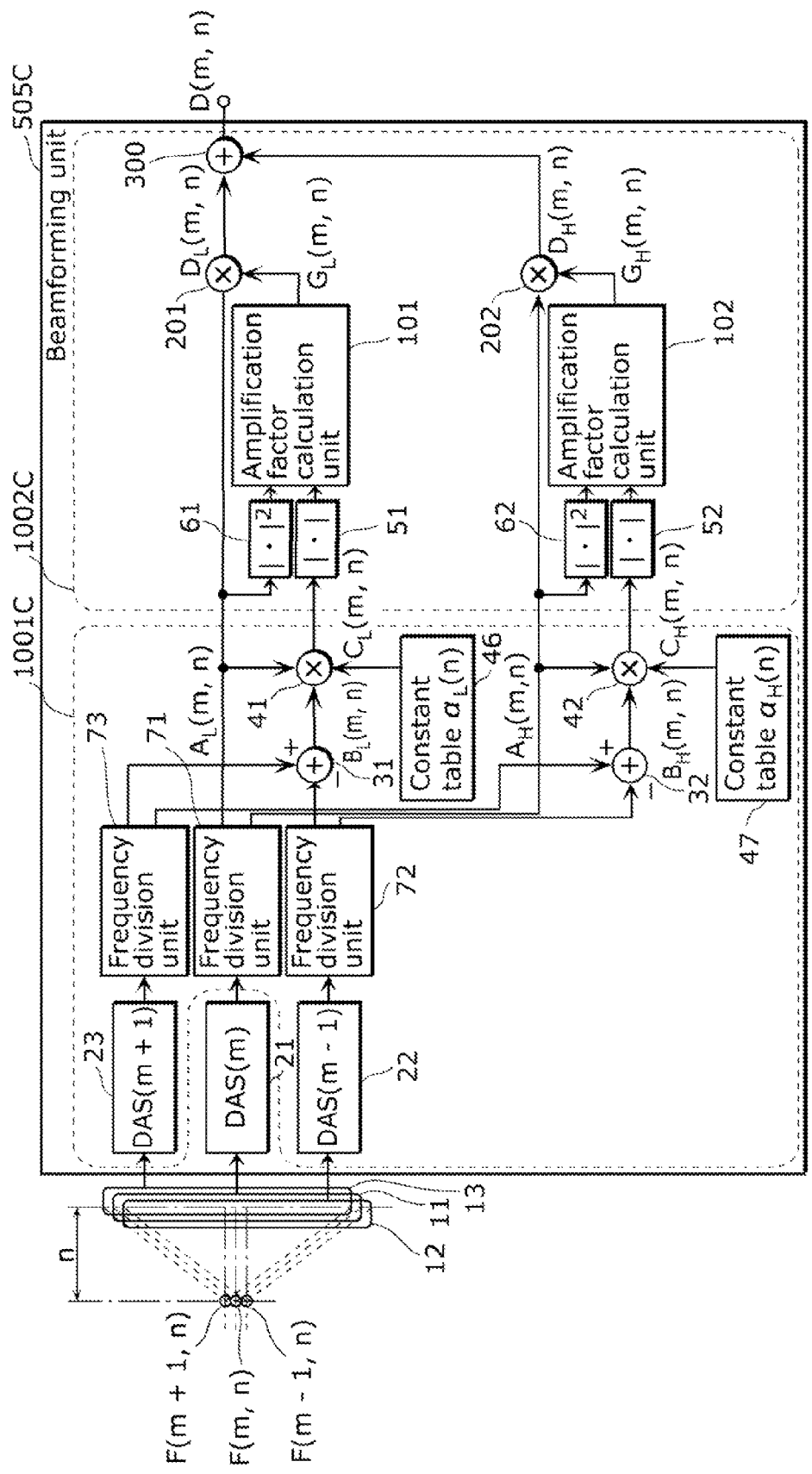
FIG. 13 is a diagram showing an example of a beamforming method according to Embodiment 3.

FIG. 13 is a block diagram of a beamforming unit 505C according to this embodiment. In FIG. 13, structural elements which are the same as structural elements included in a beamforming unit 505B in FIG. 11 are assigned the same reference signs as those in FIG. 11 and their descriptions shall be omitted.

The beamforming unit 505C according to this embodiment shown in FIG. 13 is different from the beamforming unit 505B in Embodiment 2 in two points. The first point is that, a first frequency division unit 71, a second frequency division unit 72, and a third frequency division unit 73 are additionally provided for a first DAS unit 21, a second DAS unit 22, and a third DAS unit 23, respectively in the subsequent stage. The second point is that, in a stage later than a frequency division unit (the first frequency division unit 71, the second frequency division unit 72, and the third frequency division unit 73), a processing similar to the processing performed by the beamforming unit 505B in FIG. 11 is performed for each of the divided frequencies, and a first addition unit 300 is additionally provided in which the results $D_L(m, n)$ and $D_H(m, n)$ of the processing for respective frequency bands are summed. The beamforming unit 505C includes: a sub beam generation unit 1001C including the two points described above; and a narrow beam generation unit 1002C.

In a portion in which processing is performed for each of the frequencies, correspondence between FIG. 11 and FIG. 13 is as follows. Specifically, the first subtraction unit 30 corresponds to a first low-frequency subtraction unit 31 and a first high-frequency subtraction unit 32. The first multiplication unit 40 corresponds to a first low-frequency multiplication unit 41 and a first high-frequency multiplication unit 42. The constant table 45 corresponds to a low-frequency constant table 46 and a high-frequency constant table 47. The first absolute value arithmetic unit 50 corresponds to a first low-frequency absolute value arithmetic unit 51 and a first high-frequency absolute value arithmetic unit 52. The first power arithmetic unit 60 corresponds to a first low-frequency power arithmetic unit 61 and a first high-frequency power arithmetic unit 62. The first amplification factor calculation unit 100 corresponds to a first low-frequency amplification factor calculation unit 101 and a first high-frequency amplification factor calculation unit 102. The second multiplication unit 200 corresponds to a second low-frequency multiplication unit 201 and a second high-frequency multiplication unit 202.

Operations performed by a beamforming unit having the above configuration shall be described.

Figure 14:
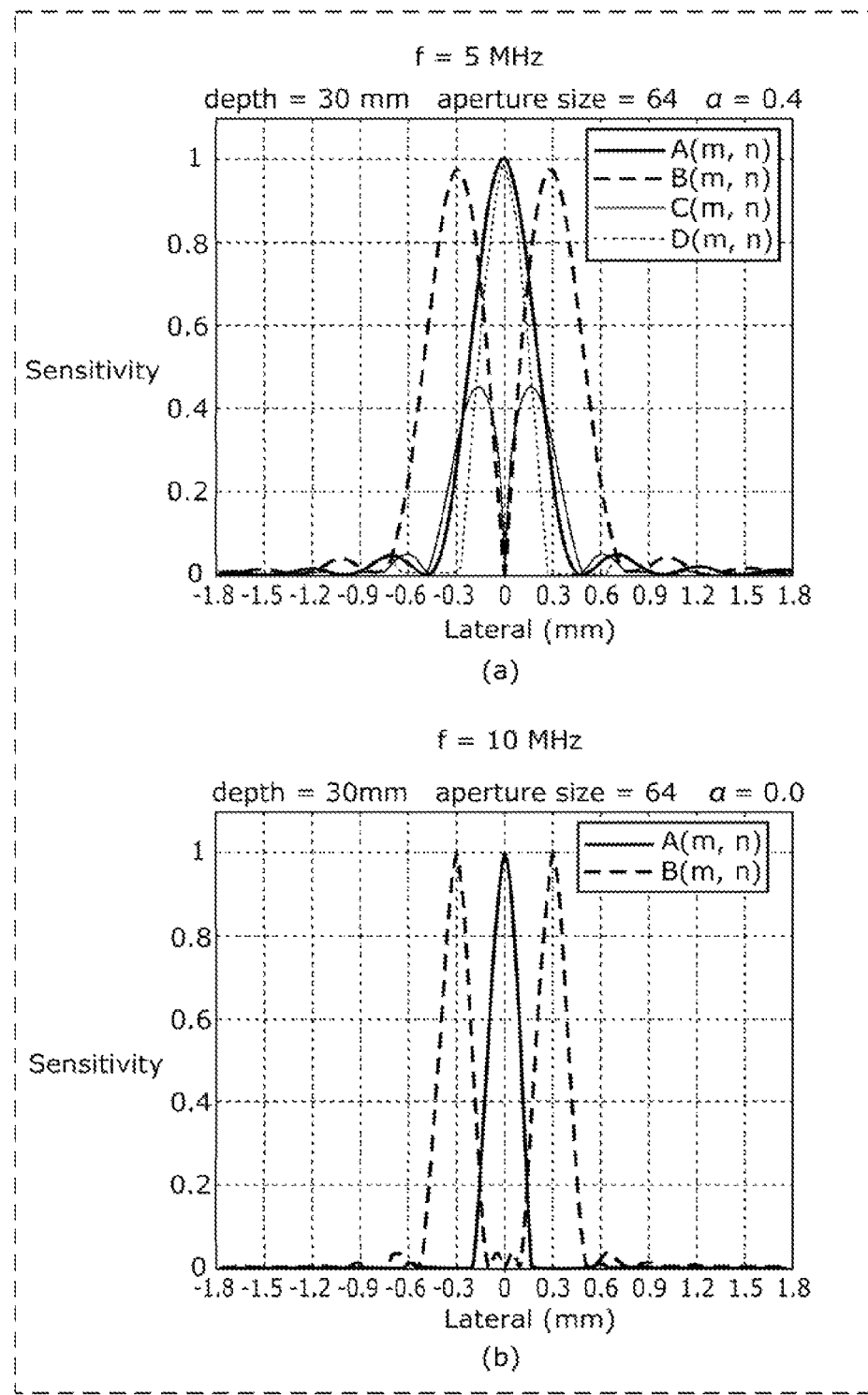
FIG. 14 shows diagrams for comparing beam patterns with different transmission frequency f.

FIG. 14 shows beam patterns of the cases in which targeted frequencies f are different.

(a) in FIG. 14 have similar conditions as the conditions for FIG. 6 to FIG. 8, and the frequency f is 5 MHz. (b) in FIG. 14 shows a beam pattern of the case in which only a frequency f is changed to 10 MHz, indicating that the beam pattern varies depending on a frequency and the beam becomes sharp when the frequency is high. The ultrasonic diagnostic apparatus transmits or receives waves of a single frequency in an approximate range of a few MHz to 10 MHz. However, in reality, pulsed waves are transmitted, a high frequency component is also included, harmonics are intentionally generated, and a harmonics distortion component is generated during propagation that is a characteristic of ultrasound waves, or the like. Thus, it is believed that, as a receiving beam, higher performance can be obtained when, rather than processing for a single frequency, processing corresponding to a wider bandwidth signal is performed. The beam pattern is different depending on the frequency, as shown in FIG. 14. Thus, processing appropriate for a broadband signal is possible by, using the additionally provided first frequency division unit 71, the second frequency division unit 72, and the third frequency division unit 73, dividing the frequencies into a plurality of frequency bands and executing, for each of the frequency bands, processing which corresponds to Embodiment 1 or Embodiment 2, and adding output signals of respective bands by using a first addition unit 300.

Note that, although this embodiment described that frequencies are divided into two bands, it is desirable that the frequencies be divided into optimal number of bands by considering trade-off against processing amount. In other words, the frequencies may be separated into three or more bands. Furthermore, the frequency division unit may perform processing, such as a filter bank, or may adopt a unit used for frequency analysis, such as fast Fourier transform (FFT).

As described above, with the beamforming method according to this embodiment, an ultrasonic diagnostic apparatus can divide ultrasound waves for each frequency of the ultrasound waves which are received from the specimen, and perform, on the divided signals, the narrowing of angle in a similar manner as above. In this manner, since the receiving sensitivity is different for each frequency of ultrasound waves, the narrowing of angle for each frequency corresponding to the receiving sensitivity can be performed.

Furthermore, with this beamforming method, an ultrasonic diagnostic apparatus can divide ultrasound waves for the respective frequencies of the ultrasound waves which are received from the specimen, and perform narrowing of angle similar to the above using a constant predetermined for each of the divided signals.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing a beamforming method according to each of the embodiments is a program described below.

The program causes a computer to execute a beamforming method for generating a beam signal from echo signals generated by a plurality of receiving elements receiving ultrasound signals reflected off a subject, the method including: generating a main beam signal by performing a delay and sum operation on receiving echo signals obtained from the receiving elements, using, as a focal point, a first region of the subject; generating, from the receiving echo signals, a sub beam signal which, compared to the main beam signal, has a low sensitivity to ultrasound signals reflected off the first region; and generating a narrow beam signal by (i) calculating a coefficient for narrowing an angle of the main beam signal, and (ii) multiplying the main beam signal by the coefficient, the coefficient being determined based on the main beam signal and the sub beam signal, wherein in the generating of a sub beam signal, the sub beam signal is generated using a differential signal that is a difference between two beam signals each of which is generated by performing a delay and sum operation on the receiving echo signals, using, as a focal point, a corresponding one of two regions of the subject which are different from the first region and are different from each other.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

A receiving method used by an ultrasonic diagnostic apparatus according to one or more exemplary embodiments disclosed herein can generate a main beam and sub beams based on a plurality of delay-and-sum outputs, and provide a sub beam pattern which is suitable for narrowing of angle of the main beam. With the narrowing of angle of the main beam, the receiving method according to one or more exemplary embodiments disclosed herein is useful for improving performance of a conventional ultrasonic diagnostic apparatus, and is particularly useful for improving image quality. Furthermore, the present invention is applicable not only to ultrasound waves but also to a sensor or the like using a plurality of array elements.

The invention claimed is:

1. A beamforming method for generating a beam signal from echo signals generated by a plurality of receiving elements receiving ultrasound signals reflected off a subject, the method comprising:
generating a main beam signal by performing a delay and sum operation on receiving echo signals obtained from a first receiving element array composed of a portion of the receiving elements, using, as a focal point, a first region of the subject;
generating a second beam signal by performing a delay and sum operation on receiving echo signals obtained from a second receiving element array that is different from the first receiving element array and composed of a portion of the receiving elements, using, as a focal point, a second region of the subject that is different from the first region;

generating a third beam signal by performing a delay and sum operation on receiving echo signals obtained from a third receiving element array that is different from the first receiving element array and the second receiving element array and composed of a portion of the receiving elements, using, as a focal point, a third region of the subject that is different from the first region and the second region;

generating a sub beam signal by using a differential signal that indicates a difference between the second beam signal and the third beam signal; and generating a narrow beam signal by (i) calculating a coefficient for narrowing an angle of the main beam signal, and (ii) multiplying the main beam signal by the coefficient, the coefficient being determined based on the main beam signal and the sub beam signal.

2. The beamforming method according to claim 1, wherein in the generating of the sub beam signal, the sub beam signal is generated by multiplying the main beam signal by the differential signal.

3. The beamforming method according to claim 1, wherein in the generating of the sub beam signal, the sub beam signal is generated by multiplying the differential signal by the main beam signal multiplied by a predetermined constant $\alpha$.

4. The beamforming method according to claim 3, wherein:
the predetermined constant $\alpha$ is determined for each distance between the first region and the first receiving element array, and
in the generating of the sub beam signal, the sub beam signal is generated by multiplying the differential signal by the main beam signal multiplied by the predetermined constant $\alpha$, using the predetermined constant $\alpha$ which is determined based on a distance between (i) the first region used when the delay and sum operation is performed in the generating of a sub beam signal and (ii) the first receiving element array, the distance being a distance when the receiving echo signals are received.

5. The beamforming method according to claim 3, further comprising receiving a user operation for changing the predetermined constant $\alpha$.

6. The beamforming method according to claim 1, further comprising:
generating partial main beam signals by dividing, based on a division frequency, the main beam signal into signals of respective frequency bands, the main beam signal being generated in the generating of the main beam; and
generating partial sub beam signals by dividing, based on the division frequency, each of the first beam signal and the second beam signal into signals of respective frequency bands,
wherein in the generating of the narrow beam signal, the narrow beam signal is generated by (i) generating partial narrow beam signals that are the narrow beam signals of respective frequency bands, and (ii) adding up the generated partial narrow beam signals, the partial narrow beam signals each being generated by using a corresponding one of the partial main beam signals as the main beam signal, and using a corresponding one of the partial sub beam signals as the sub beam signal.

7. The beamforming method according to claim 6, wherein:
a predetermined constant $\alpha$ is determined for each of the frequency bands, and in the generating of the sub beam signal, the partial sub beam signal is generated by multiplying the differential signal by the partial main beam signal multiplied by the predetermined constant $\alpha$, using the predetermined constant $\alpha$ which is determined based on the frequency band of each of the partial sub beam signals.

8. The beamforming method according to claim 1, wherein:
coordinates of a central receiving element of the first receiving element array are a midpoint between coordinates of a central receiving element of the second receiving array and coordinates of a central receiving element of the third receiving array, and
coordinates of the first region are a midpoint between coordinates of the second region and coordinates of the third region.

9. The beamforming method according to claim 1, wherein:
the receiving echo signals include a first receiving echo signal, a second receiving echo signal, and a third receiving echo signal which are received and generated by the receiving elements at a first time point, a second time point, and a third time point, respectively, the first time point, the second time point, and the third time point being three time points different from one another,
in the generating of the main beam signal, the main beam signal is generated using, as the receiving echo signals, the first receiving echo signal, and
in the generating of the sub beam signal, the sub beam signal is generated, using as the second beam signal and the third beam signal, the second receiving echo signal and the third receiving echo signal.

10. An ultrasonic diagnostic apparatus that generates a beam signal from echo signals generated by a plurality of receiving elements receiving ultrasound signals reflected off a subject, the ultrasonic diagnostic apparatus comprising:
a main beam generation unit configured to generate a main beam signal by performing a delay and sum operation on receiving echo signals obtained from a first receiving element array composed of the receiving elements, using, as a focal point, a first region of the subject;
a sub beam generation unit configured to generate (i) a second beam signal by performing a delay and sum operation on receiving echo signals obtained from a second receiving element array that is different from the first receiving element array and composed of a portion of the receiving elements, using, as a focal point, a second region of the subject that is different from the first region, (ii) a third beam signal by performing a delay and sum operation on receiving echo signals obtained from a third receiving element array that is different from the first receiving element array and the second receiving element array and composed of a portion of the receiving elements, using, as a focal point, a third region of the subject that is different from the first region and the second region, and (iii) a sub beam signal by using a differential signal that indicates a difference between the second beam signal and the third beam signal; and
a narrow beam generation unit configured to generate a narrow beam signal by (i) calculating a coefficient for narrowing an angle of the main beam signal, and (ii) multiplying the main beam signal by the coefficient, the coefficient being determined based on the main beam signal and the sub beam signal, wherein the first region, the second region, and the third region have a positional relationship such that when the third beam signal is subtracted from the second beam signal, signals are canceled out at the first region.

11. A non-transitory computer-readable recording medium having a program recorded thereon for causing a computer to execute the beamforming method according to claim 1.

* * * * *